US009012481B2

(12) United States Patent
Hahn et al.

(10) Patent No.: US 9,012,481 B2
(45) Date of Patent: Apr. 21, 2015

(54) BENZOARYLUREIDO COMPOUNDS, AND COMPOSITION FOR PREVENTION OR TREATMENT OF NEURODEGENERATIVE BRAIN DISEASE CONTAINING THE SAME

(75) Inventors: Hoh-Gyu Hahn, Seoul (KR); Kee-Dal Nam, Seoul (KR); Dong-Yun Shin, Seoul (KR); Chan-Ho Park, Incheon (KR); Sung-Woo Cho, Seoul (KR); Eun-A Kim, Gangneung-si (KR); Ghil-Soo Nam, Seoul (KR); Kyung-Il Chol, Seoul (KR); Seon-Hee Seo, Seoul (KR); Hee-Sup Shin, Uiwang-si (KR); Dong-Jin Kim, Seoul (KR); Ae-Nim Pae, Seoul (KR); Hye-Jin Chung, Seoul (KR); Hyun-Ah Choo, Seoul (KR); Hye-Whon Rhim, Seoul (KR); Yong-Seo Cho, Seoul (KR); Eun-Joo Roh, Seoul (KR); Gyo-Chang Keum, Seoul (KR); Kee-Hyun Choi, Guri-si (KR); Kye-Jung Shin, Seoul (KR); Chan-Seong Cheong, Seoul (KR); Jae-Kyun Lee, Seoul (KR); Yong-Koo Kang, Seoul (KR); Young-Soo Kim, Seoul (KR); Woong-Seo Park, Seoul (KR); Key-Sun Kim, Seoul (KR); He-Sson Chung, Incheon (KR); Chi-Man Song, Seoul (KR); Sun-Joon Min, Seoul (KR); Eunice Eun-Kyeong Kim, Seoul (KR); Cheol-Ju Lee, Seoul (KR); Soon-Bang Kang, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 784 days.

(21) Appl. No.: 13/142,313

(22) PCT Filed: Dec. 29, 2009

(86) PCT No.: PCT/KR2009/007898
§ 371 (c)(1),
(2), (4) Date: Sep. 6, 2011

(87) PCT Pub. No.: WO2010/077068
PCT Pub. Date: Jul. 8, 2010

(65) Prior Publication Data
US 2011/0319456 A1 Dec. 29, 2011

(51) Int. Cl.
C07D 235/22 (2006.01)
C07D 263/58 (2006.01)
C07D 333/06 (2006.01)
C07D 327/04 (2006.01)
C07D 277/82 (2006.01)

(52) U.S. Cl.
CPC ............ C07D 277/82 (2013.01); C07D 235/22 (2013.01); C07D 263/58 (2013.01); C07D 327/04 (2013.01); C07D 333/06 (2013.01)

(58) Field of Classification Search
None
See application file for complete search history.

(56) References Cited

U.S. PATENT DOCUMENTS 6,093,742 A    7/2000   Salituro et al.

FOREIGN PATENT DOCUMENTS

| JP | 52-3097 | 1/1977 |
| JP | 57-149280 | 9/1982 |
| JP | 58-28568 | 6/1983 |
| JP | 63-32073 | 6/1988 |
| JP | 5-320138 | 12/1993 |
| JP | 8-240873 | 9/1996 |
| JP | 2003-535887 | 12/2003 |
| JP | 2004-509949 | 4/2004 |
| KR | 10-0758214 | 9/2007 |
| WO | WO93/03022 A1 | 2/1993 |
| WO | WO01/97786 A1 | 12/2001 |
| WO | WO 01/97786 A2 | 12/2001 |
| WO | WO02/26716 A2 | 4/2002 |
| WO | WO 02/26716 A2 | 4/2002 |
| WO | 2008/006625 A2 | 1/2008 |

OTHER PUBLICATIONS

Deryk T. Loo et al., "Apoptosis is induced by β-amyloid in cultured central nervous system neurons", Proc. Natl Acad Sci USA, 1993, pp. 7951-7955.
Kathryn J. Ivins et al., "Multiple Pathways of Apoptosis in PC12 Cells", J. Bio Chem, 1992, 2107-2112.
Hui-Ming Ga et al., "Microglial activation-mediated delayed and progressive degeneration of rat nigral dopaminergic neurons: relevance to Parkinson's disease", J. Neurochem, 2002, pp. 1285-1297.
Liya Qin et al, "Microglia enhance β-amyloid peptide-induced toxicity in cortical and mesencephalic neurons by producing reactive oxygen species", Neurochem, 2002, 973-983.
Colin K. Combs et al., β-Amyloid Stimulation of Microglia and Monocytes Results in TNFa-Dependent Expression of Inducible Nitric Oxide Synthase and Nueronal Apoptosis, J. Neuroscience, 2001, pp. 1179-1188.
Luigi Puglielli, et al., "Alzheimer disease: 100 years later", Rev. Med Chil., 2001, 569-575.
David H. Small et al., "Alzheimer's disease and A β toxicity: from top to bottom", Nature Rev., 2001, 595-598.
Robert S. Wilson et al., "Person-Specific Paths of Cognitive Decline in Alzheimer's Disease and Their Relation to Age", Psychological Association, Inc., 2000, pp. 18-28.
J.T. Greenamyre et al., "Mitochondrial impairment as a cause of PD: the case of MPTP", Biochem Soc. Symp. 1999, pp. 85-97.

(Continued)

Primary Examiner — Kamal Saeed
(74) Attorney, Agent, or Firm — Goldilocks ZONE IP LAW

(57) ABSTRACT

Novel benzoarylureido compounds and a use thereof for prevention and/or treatment of the neurodegenerative brain disease are provided. The neurodegenerative brain diseases may include Alzheimer's disease, dementia, Parkinson's disease, stroke, amyloidosis, Pick's disease, Lou Gehrig's disease, Huntington's disease, Creutzfeld-Jakob disease, and the like.

10 Claims, 6 Drawing Sheets

(56) References Cited

OTHER PUBLICATIONS

Myung-Min Choi et al, "Protective effect of benzothiazole derivative KHG21834 on amyloid β-induced nerotoxicity in PC12 cells and cortical and mesencephalic neurons" Toxicology, 239, 2007, pp. 156-166.

Yuli Xie et al, "Identification of small-molecule inhibitors of the Aβ-ABAD interaction", Bioorganic & Medical Chemistry Letters 16, 2006, pp. 4657-4660.

International Search Report for PCT/KR2009/007898, Mailed Feb. 24, 2011.

"Letters to the Editor", Current Science, 1971, pp. 430-432.

Hamdy M. Abdel-Rahman et al., "Novel Benzothiazolyl Urea and Thiourea Derivatives with Potential Cytotoxic and Antimicrobial Activities", Journal of Enzyme Inhibition and Medicinal Chemistry, Feb. 22, 2007, pp. 57-64.

control | Aβ | Aβ+KHG25967

BENZOARYLUREIDO COMPOUNDS, AND COMPOSITION FOR PREVENTION OR TREATMENT OF NEURODEGENERATIVE BRAIN DISEASE CONTAINING THE SAME

CROSS REFERENCE TO RELATED APPLICATIONS

This application is a national phase application, under 35 U.S.C. 371, of international application No. PCT/KR2009/007898, filed on Dec. 29, 2009, which claimed priority to Korean Patent Application No. 10-2008-0135519, filed on Dec. 29, 2008, the disclosures of which are incorporated herein by reference.

FIELD OF THE INVENTION

The present invention relate to a novel benzoarylureido compound and a composition for the prevention and/or treatment of neurodegenerative brain diseases containing the benzoarylureido compound as an active ingredient. The neurodegenerative brain diseases may include Alzheimer's disease, dementia, Parkinson's disease, stroke (cerebral apoplexy), amyloidosis, Pick's disease, Lou Gehrig's disease, Huntington's disease, Creutzfeld-Jakob disease, and the like.

BACKGROUND OF THE INVENTION

Recently, a brain disease issues a national burden in Korea. The brain disease has taken the most dramatic increase as a cause of death in the past 10 years, but it is expected that the damage of the disease should increase rather than other diseases due to the difficulty in diagnosis and treatment.

In particular, dementia causes whole mental malfunctions such as memory impairments and a loss of skills to think, thereby ruining human life. There are various causes of dementia. 50 percent are Alzheimer's disease typed dementia, 20-30% are vascular dementia, alcoholic dementia or Parkinson's disease typed dementia, etc. and about 15-20% are Alzheimer's Disease and vascular dementia.

Alzheimer's disease (hereinafter, 'AD')-associated dementia is also called as senile dementia and starts mostly at forties. Its cause has net been exactly proven, but is revealed to closely relate with the aging.

The dementia has been reported to be caused by nervous cell damage or the decrease of acetylcholine concentration. The nervous cell damage is induced by various causes such as free radical, glutamate, excessive calcium, nitrogen, beta-amyloid protein, cytokine and the like. The nerve cell of patient with Alzheimer's disease represents neuritis plaque including excessive amount of beta-amyloid (β-Amyloid). The beta-amyloid is formed from amyloid precursor protein (hereinafter, 'APP') and produces P3 amyloid from amyloid precursor protein in normal human.

However, in case of the Alzheimer's disease, there are two hallmark disease patterns of amyloid plaque made up of beta-amyloid protein in outer part of nerve cell, and the neurofibrullary tangle (inside of nerve cell) composed of over-phosphorylated tau protein playing a crucial role in the structure of the neuron and the neurotransmission.

The excessive formation of beta-amyloid may be a representative step of starting a neurodegenerative brain disease. The aggregates of beta-amyloid in brain are considered as various toxicity in nerve cell causing neuritis plaque In vitro and in vivo experiments, the neurotoxicity of the beta-amyloid was proven to induce nerve cell apoptosis. For example, when neuron in cultured central nervous systems and nerve cell PC12 was exposed to beta-amyloid, beta-amyloid induced nerve cell apoptosis (Loo et al., *Proc Natl Acad Sci USA*, 1993, 7951-7955; Ivins et al., *J Bio Chem*, 1999, 2107-2112). beta-amyloid increased notably neurotoxicity in mesencephalic and cortical neuron in the presence of microglia. The activation of microglia and the formation of peroxide free radical increased the toxicity in nerve cell. (Gao et al., *J. Neurochem.*, 2002, 1285-1297; Qin et al., *Neurochem.*, 2002, 973-983). The brain inflammation has been widely recognized as an important cause of various neurodegenerative brain diseases including Parkinson's disease, Alzheimer's disease and the like. The inflammation-mediated degeneration of nerve cell occurs with the activation of microglia which produces various effective factors for degenerating a neuron such as eicosanoids, cytokine, reactive oxygen species, nitrogenoxide, etc. (Qin et al., *Neurochem.*, 2002, 973-983) In previous studies, the relationship between the beta-amyloid-dependent activation of microglia and various characteristics markers of neuron apoptosis in brain of patient suffered from Alzheimer's disease (Combs et al., *J Neurosci.*, 2001, 1179-1188).

Interestingly, beta-amyloid had highly-increased neurotoxicity in both of mesencephalic and cortical neuron in the presence of microglia (Gao et al., *J Neurochem.*, 2002, 1285-1297; Qin et al., *Neurochem.*, 2002, 973-983). Accordingly, APP may be accompanied with pathogenesis of other neurodegenerative brain diseases such as Parkinson's Disease as well as Alzheimer's disease (Puglielli and Kovacs, Rev Med. Chil., 2001, 569-575; Small et al., Nature Rev., 2001, 595-598). Parkinsonism symptoms also occur in a patient with Alzheimer's disease generally, and cognitive decline in patient with Alzheimer's disease was related with progression of Parkinsonism (Wilson et al., Psychol Aging, 2000, 18-28). Because dopamine neuron are known to be weak for the oxidative stress (Greenamyre et al., *Biochem Soc Symp* 1999, 85-97), the inhibition of microglia activation can be effective strategy for developing potential drug.

Accordingly, in the prevention and treatment of neurodegenerative brain disease, there are need to search and develop materials for inhibiting beta-amyloid and microglia activation.

SUMMARY OF THE INVENTION

To fulfill the need, an object of an embodiment is to provide compounds effective for prevention and/or treatment of neurodegenerative brain diseases caused by formation of beta-amyloid with low side effect, and a composition for prevention or treatment of the neurodegenerative brain diseases containing the compound.

Another object of an embodiment is to provide a use of the compounds in prevention and/or treatment neurodegenerative brain diseases, and a method of prevention and/or treatment neurodegenerative brain diseases comprising the step of administering an active amount of the compound to a patient in need thereof.

DETAILED DESCRIPTION

To achieve the objects, the present invention provides novel benzoarylureido compounds and the composition for prevention or treatment of the neurodegenerative brain diseases containing the benzoarylureido compound as active ingredients. The neurodegenerative brain diseases include Alzheimer's disease, dementia, Parkinson's disease, stroke, amyloidosis, Pick's disease, Lou Gehrig's disease, Huntington's disease, Creutzfeld-Jakob disease, and the like.

Hereinafter, the present invention will be explained in detail.

An embodiment provides a novel benzoarylureido compound. The benzoarylureido compound may have chemical structure represented by chemical formula 1:

Chemical formula 1

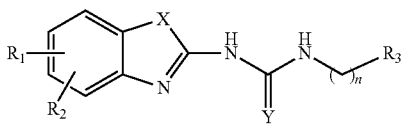

wherein, X is selected from the group consisting of S, O, NH and NCH$_3$;

Y is O or S;

R$_1$ and R$_2$ are independently selected from the group consisting of hydrogen, halogen atom, C1 to 5 linear or branched alkyl and C1 to C5 alkoxy, R$_3$ is selected from the group consisting of OH, cyano, C1 to C5 alkoxy, COOR$_4$, tetrazole, phenyl, phenyl substituted with C1 to C5 linear or branched alkyl, and phenyl substituted with C1 to C5 linear or branched alkoxy, where R$_4$ is selected from the group consisting of hydrogen, C1 to C5 linear or branched alkyl, and alkaline metals; and n is an integer ranging from 1 to 5.

In an preferred examples,

X may be selected from the group consisting of S, O, NH and NCH$_3$,

Y may be O or S,

R$_1$ and R$_2$ may be independently selected from the group consisting of H, F, Cl, C1 to C3 alkyl, and C1 to C3 alkoxy, R$_3$ may be selected from the group consisting of OH, cyano, C1 to C5 alkoxy, COOR$_4$, tetrazole, phenyl, phenyl substituted with C1 to C5 linear or branched alkyl, phenyl substituted with C1 to C5 linear or branched alkoxy, where R$_4$ is selected from the group consisting of hydrogen, C1 to C5 linear or branched alkyl, and K, and n may be an integer ranging from 1 to 3.

In another embodiment of the present invention, when n is 1,

X is O or NCH$_3$, or

Y is S, or at least one of R$_1$ and R$_2$ is halogen atom, or

R$_3$ is selected from the group consisting of OH, cyano, C1 to C5 alkoxy, COOR$_4$, tetrazole, phenyl, phenyl substituted with C1 to C5 linear or branched alkyl, and phenyl substituted with C1 to C5 linear or branched alkoxy, where R$_4$ is selected from the group consisting of hydrogen, methyl, C3 to C5 linear or branched alkyl and an alkaline metal.

In addition, when n is 2 or 3, X is S, Y is O, and R$_1$ and R$_2$ are all hydrogen, R$_3$ is selected from the group consisting of OH, cyano, C1 to C5 alkoxy, COOR$_4$, tetrazole, phenyl, phenyl substituted with C1 to C5 linear or branched alkyl, and phenyl substituted with C1 to C5 linear or branched alkoxy, where R$_4$ is selected from the group consisting of C1 to C5 linear or branched alkyl and an alkaline metal.

When X is NCH$_3$, Y is S, or at least one of R$_1$ and R$_2$ is selected from the group consisting of halogen atom, C1 to C5 linear or branched alkyl and C1 to C5 alkoxy.

When X and Y are all S, at least one of R$_1$ and R$_2$ is selected from the group consisting of halogen atom, C1 to C5 linear or branched alkyl, and C1 to C5 alkoxy, or R$_3$ is selected from the group consisting of phenyl, phenyl substituted with C1 to C5 linear or branched alkyl, phenyl substituted with C1 to C5 linear or branched alkoxy, cyano, C1 to C3 alkoxy, tetrazole, OH and COOR4 (where, R4 is selected from the group consisting of hydrogen, methyl, C3 to C5 linear or branched alkyl, and K).

The present inventors synthesized many benzoarylureido compounds and tested them on cultured PC12 cell and mesencephalic and cortical neuron-microglia, while researching an effective protecting agent against nervous cell apoptosis induced by beta-amyloid. As a result, it was found that the benzoarylureido compounds represented by chemical formula 1 had excellent inhibiting activity on beta-amyloid synthesis and activation of microglia, and good protecting activity of the nervous cell.

To test benzoarylureido compounds can protect the nervous cell or not, TUNEL (In situ transferase-mediated dUTP nick end labeling) labeling method, and immunobiochemical analysis for degeneration of nerve cell using are used. Also, there are various analyzing methods for test the protecting activities of benzoarylureido compounds such as the decrease rate of Dopamine and/or GABA (γ-aminobutyrate) which causes epilepsy, convulsion, attack, and etc. extend of phosphorylation of ERK (Extracellular signal-regulated kinase), Immunohistochemical staining of MAP-2 (microtubule-associated proteins), and/or LDH (lactate dehydrogenase) release assay.

GABA is a representative neurotransmitting amino acid in synapse suppressing excitation and is at a high concentration (30 mM) in central nerve system of the whole body. The recovery of GABA concentration from reduced state induced by beta-amyloid means that the concentration of GABA can function normally the neurotransmitter. That is, the brain recovers the normal function. The weakened of decrease in absorption of dopamine which happens largely in dopamine neuron can be explained just as GABA does. Accordingly, the protecting activity the novel compound can be evaluated by measuring the GABA and/or dopamine.

Further, ERK phosphorylation is a part of signal transduction systems in cell apoptosis, and ERK can be activated (phosphorylated) due to extracellular stimulation or intracellular cell apoptosis. Thus, the ERK phosphorylation can be used for indicator of nerve cell apoptosis. MAP-2 staining method can be marker for cell damage in morphological change of cortical nerve cell or nerve cell process. When cellular membrane is damaged, the cell damage and nerve cell apoptosis can be measured by LDH analysis using LDH extracellular release.

As a result of measuring benzoarylureido compounds represented by chemical formula 1 according to the analyzing method, the present invention confirmed that they prevented and treated nerve cell apoptosis or modification which directly causes the neurodegenerative brain diseases. Another embodiment provides a composition for prevention and/or treatment of the neurodegenerative brain disease comprising at least one of the compounds represented by chemical formula 1 and/or pharmaceutically-acceptable salts thereof as an active ingredient. Alternatively, an embodiment provides a use of at least one of the compounds represented by chemical formula 1 and/or pharmaceutically-acceptable salts thereof in prevention and/or treatment of the neurodegenerative brain disease. Alternatively, an embodiment of provides a method of prevention and/or treatment of the neurodegenerative brain disease comprising the step of administering an active amount of at least one of the compounds represented by chemical formula 1 and/or pharmaceutically-acceptable salts thereof to a patient in need thereof. The patient may be a mammal, such as human, suffering from or having risk of the neurodegenerative brain disease and/or in need of treatment or prevention of the neurodegenerative brain disease.

In a still further embodiment, a food composition for prevention or improvement of the neurodegenerative brain disease comprising at least one of the compounds represented by chemical formula 1 and pharmaceutically-acceptable salts thereof is provided.

The neurodegenerative brain diseases include Alzheimer's disease, dementia, Parkinson's disease, stroke, amyloidosis, Pick's disease, Lou Gehrig's disease, Huntington's disease, Creutzfeld-Jakob disease, and the like.

The composition for prevention or treatment of the neurodegenerative brain diseases according to the present invention may contain the active compound with or without other pharmaceutically acceptable drugs, carriers, or excipients. The amount of the benzoarylureido compound contained in the composition according to the present invention may be approximately 0.1 to 99 wt %, but more preferably, properly controlled according to its usage.

The carriers and excipients used in the present invention may be properly selected depending on the intended formulation type of the composition, for example, including conventional diluents, fillers, expanders, wetting agents, disintegrants, and/or surfactants. Representative diluents or excipients may include water, dextrin, calcium carbonate, lactose, propylene glycol, liquid paraffin, talc, isomerized sugar, sodium metabisulfite, methylparaben, propylparaben, magnesium stearate, milk sugar, normal saline, flavorings and colorants.

The composition according to the present invention may be used as drugs, food additives, or food. When the composition is used as drugs, the composition may be administered in oral or parenteral pathway. The formulation type of the composition may vary depending on its usage. For example, the composition may be formulated in the form of plasters, granules, lotions, powders, syrups, liquids, solutions, aerosols, ointments, fluidextracts, emulsions, suspensions, infusions, tablets, injections, capsules, pills, and the like.

The administration dosage may be determined considering age, sexuality and condition of patient, absorption and inactivation rates in the body of the active ingredient, and co-administered drugs. For example, the dosage of the composition may be 1 mg/kg (body weight) to 500 mg/kg based on the active ingredient.

The composition for prevention or treatment of the neurodegenerative brain disease according to the present invention contains an arylureido acetate compound preventing the degeneration and damage of brain cell which are caused by beta-amyloid. Thus, the composition of the present invention has an effect of prevention and treatment of the neurodegenerative brain diseases with low cytotoxicity.

BRIEF DESCRIPTION OF THE DRAWINGS

FIG. 1A is a microscope analysis result and FIG. 1B is a quantitative analysis result of cell survival rate in MTT assay Control: treatment of 5% DMSO without beta-amyloid for 26 hours, Ab: treatment with addition of 5% DMSO for 24 hours after treatment of beta-amyloid 50 μM for 2 hours, Ab+KHG25967: treatment with addition of KHG25967 50 nM dissolved in 5% DMSO for 24 hours after treatment of beta-amyloid 5004 for 2 hours.

FIG. 2A is results of immunoblotting assay of phosphoryled-ERK1, phosphoryled-ERK2, ERK1, ERK2 and cleaved caspase 3, FIG. 2B is a quantitative analysis result of p-ERK, FIG. 2C is a quantitative analysis result of caspase 3 compared to FIG. 2a and the condition of each lane is the same as FIG. 1.

FIG. 3A is a quantitative analysis result of interleukin-1beta which shows relative percent value compared to 100 percent of reacting result of LPS treatment, and FIG. 3B is a quantitative analysis result of tumor necrosis factor-alpha which relative percent value compared to 100 percent of reacting result of LPS treatment.

Control: treatment of 5% DMSO for 6 hours after treatment of PBS for 2 hours,

LPS: treatment of 5% DMSO for 6 hours after pre-treatment of LPS 1 μg/ml dissolved in PBS for 2 hours, and LPS+KHG25967: treatment of KHG25967 50 nM dissolved in 5% DMSO for 6 hours after pre-treatment of LPS 1 μg/ml dissolved in PBS for 2 hours.

Figure 4A:
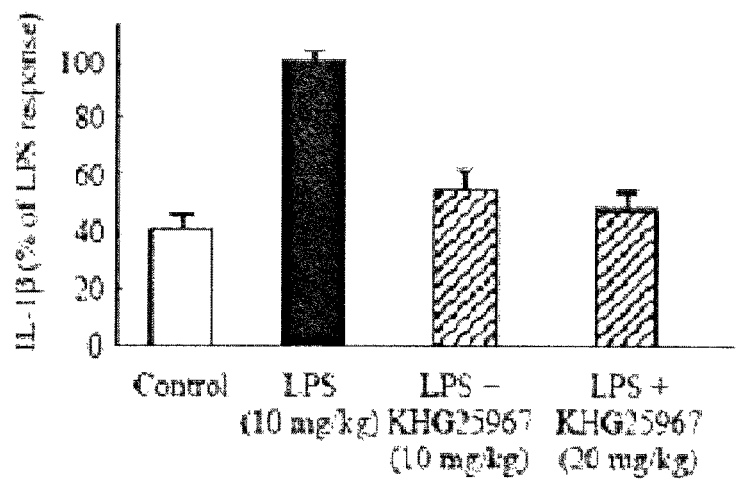
Figure 4B:
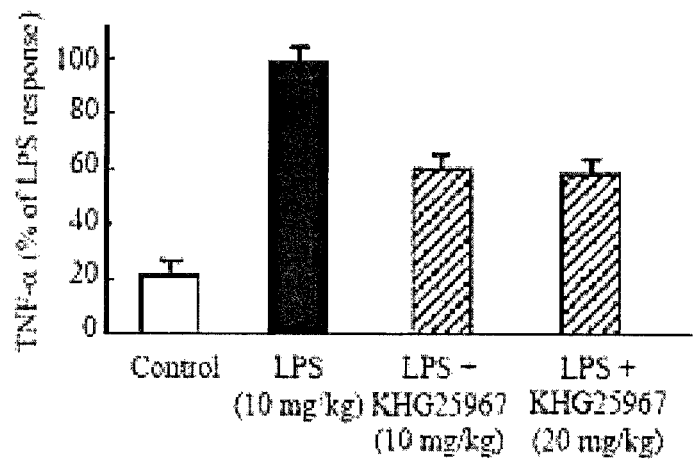
Figure 4C:
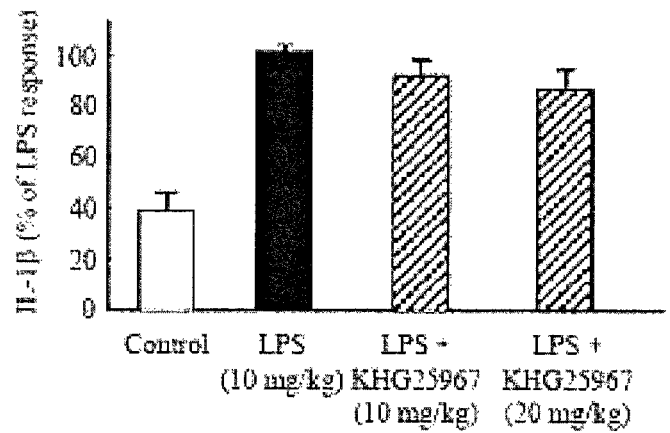
Figure 4D:
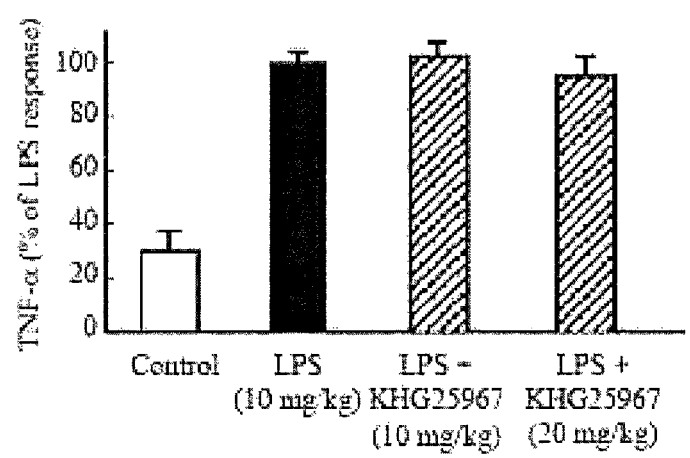

FIGS. 4A to 4D represent the effect of compound KHG25967 against cytokine change induced by LPS in brain and blood serum of C57BL/6 mice; FIG. 4A and FIG. 4B are the quantitative analysis results of interleukin-1beta and tumor necrosis factor-alpha in brain, and FIGS. 4C and 4D are the quantitative analysis results of interleukin-1beta and tumor necrosis factor-alpha in blood serum.

Control: treatment of PBS for 6 hours after administration of only 5% DMSO for 2 weeks, LPS: treatment of LPS 10 mg/kg dissolved in PBS for 6 hours after administration of only 5% DMSO for 2 weeks, LPS+KHG25967 treatment of LPS 10 mg/kg dissolved in PBS after oral administration of KHG25967 (10 mg/kg or 20 mg/kg) dissolved in 5% DMSO one a day for 2 weeks.

EXAMPLES

The present invention is further explained in more detail with reference to the following examples. These examples, however, should not be interpreted as limiting the scope of the present invention in any manner.

Preparation Example

Synthesis of KHG25967 [2-(3-benzo[d]thiazole-2-yl ureido)acetic acid]

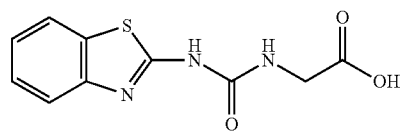 [SMILES: O=C(O)CNC(=O)Nc1nc2ccccc2s1]

The compound was synthesized by hydrolysis method. 100 mg of ethyl 2-(3-benzo[d]thiazole-2-ylureido)acetate and 60 mg of KOH were added to 10 ml of water, and subjected to reflux under 100° C. for 2 hours. The obtained reaction mixture were stirred at room temperature for 30 minutes, and cooled in ice-bath. Then, 1 ml of strong hydrochloric acid was added thereto, to acidify the obtained reaction mixture. 74 mg of 2-(3-benzo[d]thiazole-2-ylureido)acetic acid was produced in white solid phase.

KHG26027

Synthesis of [ethyl 3-(3-1H-benzo[d]imidazole-2-ylureido)propanoate]

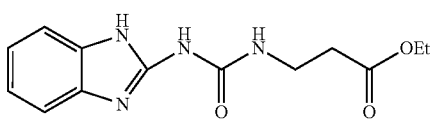 [SMILES: CCOC(=O)CCNC(=O)Nc1nc2ccccc2[nH]1]

The compound was synthesized by esterification method. 2-amino-benzimidazole (0.162 g, 1.22 mmol) was dissolved in 3 mL of tetrahydrofuran. To the solution, ethyl 3-isocyanatopropinonate (0.174 g, 0.16 mL, 1.22 mmol) was added, and subjected to reflux at 66° C. for 40 minutes. The obtained reaction mixture was cooled to room temperature, and then the obtained precipitate was filtrated, to produce white solid in the amount of 79 mg.

KHG26096

Synthesis of [potassium 2-(3-benzo[d]thiazole-2-ylureido)acetate]

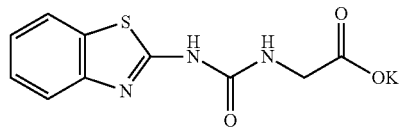

The exemplary alkali metal salt compound according to the present invention was synthesized as shown in reaction scheme 1-1.

2-(3-benzo[d]thiazole-2-ylureido)acetic acid (0.26 mmol, 70 mg) was added to 0.55 ml of an aqueous solution dissolving 15 mg of KOH, stirred at room temperature for 2 hours, and filtrated using Millepore Sterivex-GV (0.22 um filter unit). Solvent was removed by using a freeze dryer, to produce white solid in the amount of 64 mg (yield 80%).

KHG26342

Synthesis of [N-(benzo[d]thiazole-2-yl)-2-cyanoacetamide]

The compound having thiazole group according to the present invention was synthesized as shown in Reaction Scheme 1-2.

(Reaction Scheme 1-2)

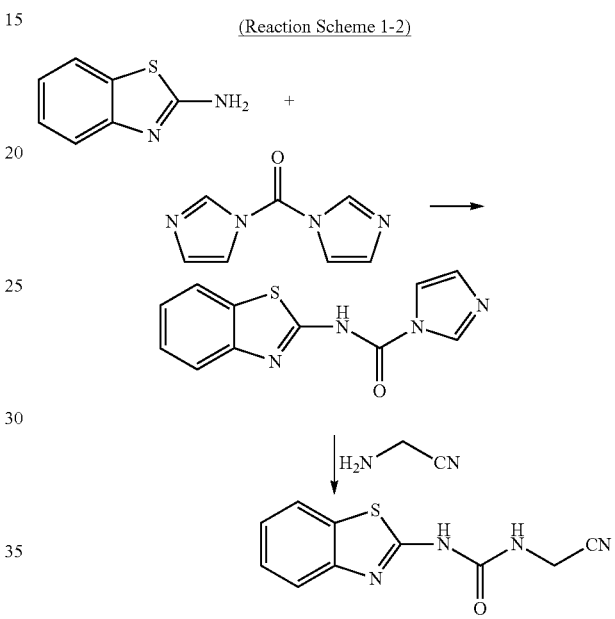

0.3 g of benzothiazole was dissolved in 50 ml of tetrahydrofuran, and then 0.32 g of carbodiimide was added thereto in a dropwise manner in ice-bath. The obtained reaction mixture was stirred at room temperature for 10 hours. The produced white solid was filtrated, to obtain N-(benzo[d]thiazole-2-yl)-1H-imidazole-1-carboxamide (0.261 g, 54%).

(Reaction scheme 1-1)

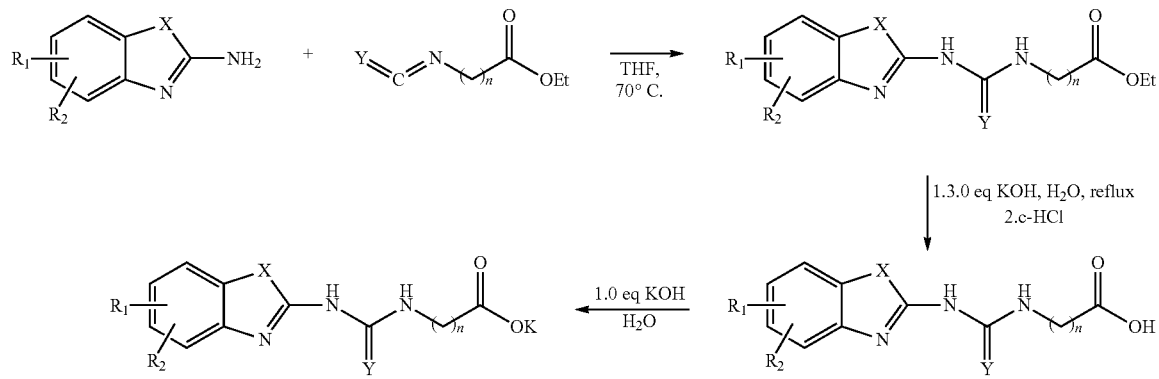

n = 1, 2, 3
X = S, N, N(CH$_3$)
Y = S, O

N-(benzo[d]thiazole-2-yl)-1H-imidazole-1-carboxamide (30 mg) was dissolved in 5 ml of tetrahydrofuran, and 11.1 mg of 2-aminoacetonitrile and then 29 μl of acetic were added thereto in a dropwise manner. The obtained reaction mixture was stirred at 30° C. for 18 hours, to produce N-(benzo[d]thiazole-2-yl)-2-cyanoacetamide (10 mg) in a light brown solid phase

KHG26345

Synthesis of [N-(benzo[d]thiazole-2-yl)-2-(2H-tetrazole-5-yl)acetamide]

The compound having thiazole group according to the present invention was synthesized as shown in Reaction Scheme 1-3.

(Reaction Scheme 1-3)

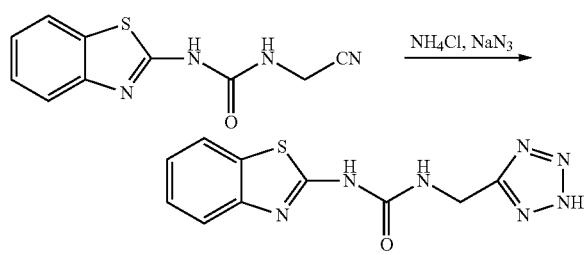

N-(benzo[d]thiazole-2-yl)-2-cyanoacetamide (0.1 g), $NH_4Cl$ (5.0 eq, 0.1 g), and $NaN_3$ (5.2 eq, 0.13 g) were dissolved on 2.1 mL of DMF (dimethylformamide), and heated at 120° C. for 6 hours. DMF was removed under reduced pressure distillation, and 10 ml of water and 5% NaOH solution were added thereto. The aqueous layer was washed with 15 ml of $Et_2O$, and treated with activated carbon. To the obtained reaction mixture, 10% aqueous hydrochloric acid, making the solution with pH 2. The obtained reaction mixture was extracted with methylene chloride, to produce N-(benzo[d]thiazole-2-yl)-2-(2H-tetrazole-5-yl)acetamide (20%, 21 mg) in light yellow solid phase.

The compounds shown in Table 1 were produced by the same method as described above.

TABLE 1

| Number of Compound | X | Y | $R_1$ & $R_2$ | $(CH_2)_n R_3$ |
|---|---|---|---|---|
| KHG25948 | S | O | H, H | $CH_2C_6H_4$ (4-$CH_3$) |
| KHG25954 | S | O | H, H | $CH_2CO_2$(n-Bu) |
| KHG25956 | S | O | 6-F, H | $CH_2CO_2Et$ |
| KHG25967 | S | O | H, H | $CH_2CO_2H$ |
| KHG25989 | O | O | 6-Cl, H | $CH_2CO_2Et$ |
| KHG25990 | O | O | 6-Cl, H | $CH_2C_6H_4$ (4-$CH_3$) |
| KHG26004 | S | O | H, H | $CH_2CH_2CH_2CO_2Et$ |
| KHG26005 | S | O | H, H | $CH_2CH_2CO_2Et$ |
| KHG26019 | S | O | 6-$OCH_3$, H | $CH_2CO_2Et$ |
| KHG26025 | S | O | H, H | $CH_2CH_2CH_2CO_2H$ |
| KHG26026 | S | O | H, H | $CH_2CH_2CO_2H$ |
| KHG26027 | NH | O | H, H | $CH_2CH_2CO_2Et$ |
| KHG26028 | NH | O | H, H | $CH_2CH_2CH_2CO_2Et$ |
| KHG26029 | $NCH_3$ | O | H, H | $CH_2CO_2Et$ |
| KHG26030 | $NCH_3$ | O | H, H | $CH_2CH_2CO_2Et$ |
| KHG26031 | $NCH_3$ | O | H, H | $CH_2CH_2CH_2CO_2Et$ |
| KHG26096 | S | O | H, H | $CH_2CO_2K$ |
| KHG26172 | $NCH_3$ | O | H, H | $CH_2CO_2K$ |
| KHG26175 | S | O | 6-$OCH_3$, H | $CH_2CO_2K$ |
| KHG26176 | S | O | 6-OEt, H | $CH_2CO_2K$ |
| KHG26177 | S | O | 6-Cl, H | $CH_2CO_2K$ |
| KHG26178 | S | O | 4-Cl, H | $CH_2CO_2K$ |
| KHG26180 | S | O | 5-$CH_3$, 6-$CH_3$ | $CH_2CO_2K$ |
| KHG26216 | S | O | 6-$CH_3$, H | $CH_2CO_2K$ |
| KHG26217 | S | O | 4-$CH_3$, H | $CH_2CO_2K$ |
| KHG26220 | S | O | H, H | $CH_2CH_2CO_2K$ |
| KHG26221 | S | O | H, H | $CH_2CH_2CH_2CO_2K$ |
| KHG26222 | $NCH_3$ | O | H, H | $CH_2CH_2CO_2K$ |
| KHG26223 | $NCH_3$ | O | H, H | $CH_2CH_2CH_2CO_2K$ |
| KHG26279 | S | O | H, H | $CH_2CH_2OH$ |
| KHG26280 | $NCH_3$ | O | H, H | $CH_2CO_2H$ |
| KHG26303 | $NCH_3$ | S | H, H | $CH_2CO_2Et$ |
| KHG26304 | S | S | H, H | $CH_2CO_2Et$ |
| KHG26305 | S | S | 6-$CH_3$, H | $CH_2CO_2Et$ |
| KHG26306 | S | S | 4-$CH_3$, H | $CH_2CO_2Et$ |
| KHG26307 | S | S | 5-$CH_3$, 6-$CH_3$ | $CH_2CO_2Et$ |
| KHG26308 | S | S | 6-$OCH_3$, H | $CH_2CO_2Et$ |
| KHG26309 | S | S | 6-OEt, H | $CH_2CO_2Et$ |
| KHG26310 | S | S | 6-F, H | $CH_2CO_2Et$ |
| KHG26311 | S | S | 6-Cl, H | $CH_2CO_2Et$ |
| KHG26312 | S | S | 4-Cl, H | $CH_2CO_2Et$ |
| KHG26316 | S | S | H, H | $CH_2CO_2H$ |
| KHG26332 | S | O | H, H | $CH_2CH_3$ |
| KHG26334 | $NCH_3$ | S | H, H | $CH_2CO_2H$ |
| KHG26335 | S | S | 5-$CH_3$, 6-$CH_3$ | $CH_2CO_2H$ |
| KHG26336 | S | S | 6-OEt, H | $CH_2CO_2H$ |
| KHG26340 | S | S | 4-$CH_3$, H | $CH_2CO_2H$ |
| KHG26341 | S | S | 6-Cl, H | $CH_2CO_2H$ |
| KHG26342 | S | O | H, H | $CH_2CN$ |
| KHG26344 | S | O | H, H | $CH_2CH_2OEt$ |
| KHG26345 | S | O | H, H | $CH_2$-tetrazolyl |
| KHG26346 | S | O | 6-$OCH_3$, H | $CH_2CO_2H$ |
| KHG26347 | S | O | 6-OEt, H | $CH_2CO_2Et$ |
| KHG26348 | S | O | 6-OEt, H | $CH_2CO_2H$ |
| KHG26349 | S | O | 6-Cl, H | $CH_2CO_2Et$ |
| KHG26350 | S | O | 6-Cl, H | $CH_2CO_2H$ |
| KHG26351 | S | O | 4-Cl, H | $CH_2CO_2Et$ |
| KHG26352 | S | O | 4-Cl, H | $CH_2CO_2H$ |
| KHG26353 | S | O | 5-$CH_3$, 6-$CH_3$ | $CH_2CO_2Et$ |
| KHG26354 | S | O | 5-$CH_3$, 6-$CH_3$ | $CH_2CO_2H$ |
| KHG26355 | S | O | 6-$CH_3$, H | $CH_2CO_2H$ |
| KHG26356 | S | O | 4-$CH_3$, H | $CH_2CO_2H$ |
| KHG26357 | $NCH_3$ | O | H, H | $CH_2CH_2CO_2H$ |
| KHG26358 | $NCH_3$ | O | H, H | $CH_2CH_2CH_2CO_2H$ |

Identifying Data

KHG25948

Synthesis of 1-(benzo[d]thiazole-2-yl)-3-(4-methylbenzyl)urea

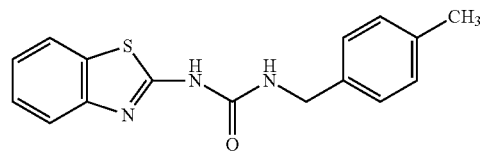 [SMILES: Cc1ccc(CNC(=O)Nc2nc3ccccc3s2)cc1]

yield: 73% mp: 257° C.

$^1$H NMR (300 MHz, $CDCl_3$) δ 10.75 (s, 1H, NH), 7.88 (d, 1H, $^3J$=7.83 Hz, NH), 7.13-7.62 (m, 8H, Ar—H), 4.32 (d, 2H, $^3J$=5.73 Hz, $CH_2$), 2.27 (s, 3H, $CH_3$).

KHG25954

Synthesis of butyl 2-(3-benzo[d]thiazole-2-ylureido)acetate

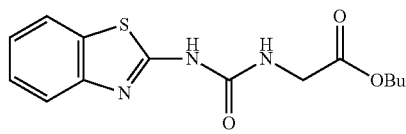

yield: 8% mp 294° C.

$^1$H NMR (300 MHz, DMSO-d$_6$) δ 11.01 (brs, 1H, NH), 7.88-7.19 (m, 4H, Ar—H), 7.09 (brs, 1H, NH), 4.09 (t, 2H, $^3$J=7.2 Hz, OCH$_2$CH$_2$CH$_2$CH$_3$), 3.97 (d, 2H, $^3$J=5.7 Hz, CH$_2$), 1.57 (q, 2H, $^3$J=7.2 Hz, OCH$_2$CH$_2$CH$_2$CH$_3$), 1.34 (m, 2H, $^3$J=7.2 Hz, OCH$_2$CH$_2$CH$_2$CH$_3$), 0.88 (t, 3H, $^3$J=7.2 Hz, OCH$_2$CH$_2$CH$_2$CH$_3$).

KHG25956

Synthesis of ethyl 2-(3-(6-fluorobenzo[d]thiazole-2-yl)ureido)acetate

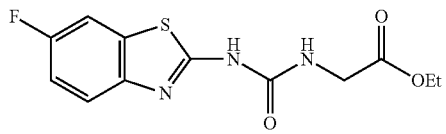 [SMILES: CCOC(=O)CNC(=O)Nc1nc2ccc(F)cc2s1]

yield: 30% mp: 291° C.

$^1$H NMR (300 MHz, DMSO-d$_6$) δ 11.05 (brs, 1H, NH), 7.82-7.17 (m, 3H, Ar—H), 7.04 (brs, 1H, NH), 4.13 (q, 2H, $^3$J=7.2 Hz, OCH$_2$CH$_3$), 3.96 (d, 2H, $^3$J=5.7 Hz, CH$_2$), 1.21 (t, 3H, $^3$J=7.2 Hz, OCH$_2$CH$_3$)

KHG25967

Synthesis of 2-(3-benzo[d]thiazole-2-ylureido)acetic acid

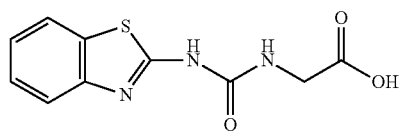 [SMILES: O=C(O)CNC(=O)Nc1nc2ccccc2s1]

yield: 85% mp: 217° C.

$^1$H NMR (300 MHz, DMSO-d$_6$) δ 7.18-7.89 (m, 4H, ArH), 7.01 (t, 1H, $^3$J=5.7 Hz, NH), 3.89 (d, 2H, $^3$J=5.7 Hz, CH$_2$).

KHG25989

Synthesis of ethyl 2-(3-(6-chlorobenzo[d]oxazole-2-yl)ureido)acetate

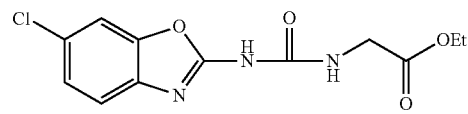 [SMILES: CCOC(=O)CNC(=O)Nc1nc2ccc(Cl)cc2o1]

yield: 21% mp: 225° C.

$^1$H NMR (300 MHz, DMSO-d$_6$) δ 11.42 (brs, 1H, NH), 8.55 (brs, 1H, NH), 7.62-7.23 (m, 3H, Ar—H), 4.12 (q, 2H, $^3$J=7.1 Hz, CH$_2$), 4.05 (d, 2H, $^3$J=5.5 Hz, CH$_2$), 1.21 (t, 3H, $^3$J=7.1 Hz, CH$_3$).

KHG25990

Synthesis of Ethyl 2-(3-(6-chlorobenzo[d]oxazole-2-yl)ureido)acetate

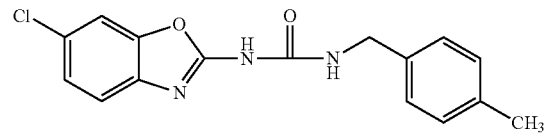 [SMILES: Cc1ccc(CNC(=O)Nc2nc3ccc(Cl)cc3o2)cc1]

yield: 31% mp: 233° C.

$^1$H NMR (300 MHz, DMSO-d$_6$) δ 11.31 (brs, 1H, NH), 8.61 (brs, 1H, NH), 7.61-7.14 (m, 3H, Ar—H), 4.43 (d, 2H, $^3$J=6.0 Hz, CH$_2$), 2.07 (s, 3H, CH$_3$).

KHG26004

Synthesis of ethyl 4-(3-benzo[d]thiazole-2-ylureido)butanoate

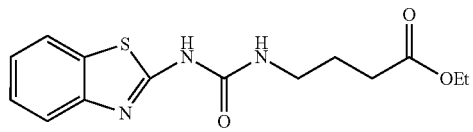 [SMILES: CCOC(=O)CCCNC(=O)Nc1nc2ccccc2s1]

yield: 56% mp: 278° C.

$^1$H NMR (300 MHz, DMSO-d$_6$) δ 10.65 (s, 1H, NH), 7.87-7.17 (m, 4H, Ar—H), 6.80 (brs, 1H, NH), 4.05 (q, 2H, $^3$J=6.0 Hz, OCH$_2$CH$_3$), 3.16 (q, 2H, $^3$J=6.0 Hz, CH$_2$CH$_2$CH$_2$), 2.33 (t, 2H, $^3$J=9.0 Hz, CH$_2$CH$_2$CH$_2$), 1.77-1.67 (m, 2H, $^3$J=6.0 Hz, CH$_2$CH$_2$CH$_2$), 1.17 (t, 2H, $^3$J=6.0 Hz, OCH$_2$CH$_3$).

KHG26005

Synthesis of ethyl 3-(3-benzo[d]thiazole-2-ylureido)propanoate

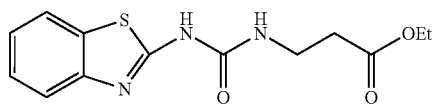 [SMILES: CCOC(=O)CCNC(=O)Nc1nc2ccccc2s1]

yield: 89% mp: 256° C.

$^1$H NMR (300 MHz, DMSO-d$_6$) δ 10.76 (s, 1H, NH), 7.90-7.20 (m, 4H, Ar—H), 6.92 (t, 1H, $^3$J=6.0 Hz, NH), 4.11 (q, 2H, $^3$J=6.3 Hz, OCH$_2$CH$_3$), 3.42 (q, 2H, $^3$J=6.3 Hz, CH$_2$), 2.56 (t, 2H, J=6.3 Hz, CH$_2$), 1.22 (t, 2H, $^3$J=7.2 Hz, OCH$_2$CH$_3$).

KHG26019

Synthesis of ethyl 2-(3-(6-methoxybenzo[d]thiazole-2-yl)ureido)acetate

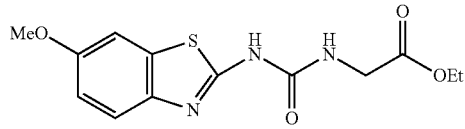 [SMILES: CCOC(=O)CNC(=O)Nc1nc2ccc(OC)cc2s1]

yield: 79% mp: 281.9° C.

$^1$H NMR (300 MHz, DMSO-d$_6$) δ 10.86 (s, 1H, NH), 7.53-6.93 (m, 3H, Ar—H), 7.03 (brs, 1H, NH), 4.13 (q, 2H, $^3$J=7.2 Hz, OCH$_2$CH$_3$), 3.95 (d, 2H, $^3$J=5.7 Hz, CH$_2$), 3.32 (s, 3H, OCH$_3$), 1.21 (t, 3H, $^3$J=7.2 Hz, OCH$_2$CH$_3$).

KHG26025

Synthesis of 4-(3-benzo[d]thiazole-2-ylureido)butanoic acid

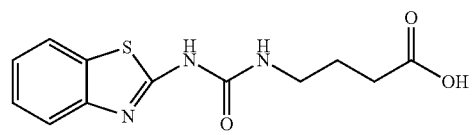 [SMILES: O=C(O)CCCNC(=O)Nc1nc2ccccc2s1]

yield: 99% mp: 210° C.

$^1$H NMR (300 MHz, DMSO-d$_6$) δ 10.6 (brs, 2H, NH, COOH), 7.88-7.18 (m, 4H, Ar—H), 6.88 (t, 1H, J=5.4 Hz, NH), 3.18 (q, 2H, $^3$J=6.6 Hz, CH$_2$CH$_2$CH$_2$), 2.27 (t, 2H, $^3$J=7.4 Hz, CH$_2$CH$_2$CH$_2$), 1.75-1.65 (m, 2H, CH$_2$CH$_2$CH$_2$).

KHG26026

Synthesis of 3-(3-benzo[d]thiazole-2-ylureido)propanic acid

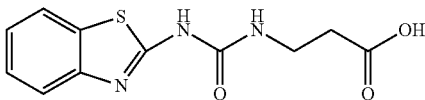

yield: 70% mp: 243° C.

$^1$H NMR (300 MHz, DMSO-d$_6$) δ 7.17-7.87 (m, 4H, ArH), 6.89 (t, 1H, $^3$J=5.5 Hz, NH), 3.35 (m, 2H, CH$_2$), 2.47 (m, 2H, CH$_2$).

KHG26027

Synthesis of ethyl 3-(3-1H-benzo[d]imidazole-2-ylureido)propanoate

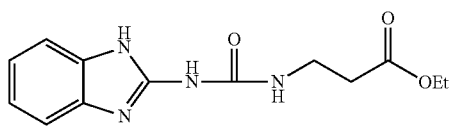 [SMILES: CCOC(=O)CCNC(=O)Nc1nc2ccccc2[nH]1]

yield: 23% mp: 264° C.

$^1$H NMR (300 MHz, DMSO) δ 11.33 (s, 1H, NH), 9.89 (s, 1H, NH), 7.34 (s, 1H, NH), 7.25 (s, 2H, Ar—H), 6.99-7.02 (m, 2H, Ar—H), 4.05-4.12 (q, 2H, $^2$J=6.9 Hz, $^3$J=14.1 Hz, ethyl-CH$_2$), 3.37-3.46 (q, 2H, $^2$J=11.1 Hz, $^3$J=17.7 Hz, CH$_2$), 2.52-2.57 (t, 2H, $^2$J=6.6 Hz, $^3$J=13.2 Hz, CH$_2$), 1.19 (t, 3H, $^2$J=7.2 Hz, $^3$J=14.1 Hz, ethyl-CH$_3$).

KHG26028

Synthesis of ethyl 4-(3-1H-benzo[d]imidazole-2-ylureido)butanoate

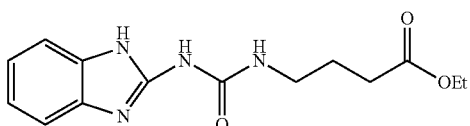

yield: 16% mp: 277° C.

$^1$H NMR (300 MHz, CDCl$_3$) δ 7.30 (s, 2H, Ar—H), 7.04-7.07 (m, 2H, Ar—H), 4.03-4.10 (q, 2H, $^2$J=6.9 Hz, $^3$J=15.6 Hz, ethyl-CH$_2$), 3.26-3.33 (q, 2H, $^2$J=6.9 Hz, $^3$J=13.5 Hz, CH$_2$), 2.31-2.36 (t, 2H, $^2$J=7.8 Hz, $^3$J=15.0 Hz, CH$_2$), 1.85-

1.92 (m, 2H, $^2J$=12.0 Hz, $^3J$=19.2 Hz, CH$_2$), 1.19 (t, 3H, $^2J$=7.2 Hz, $^3J$=14.4 Hz, ethyl-CH$_3$).

KHG26029

Synthesis of ethyl 2-(3-(1-methyl-1H-benzo[d]imidazole-2-yl)ureido)acetate

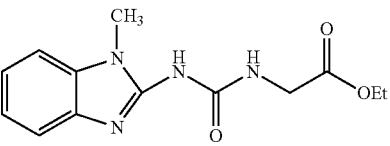 [SMILES: CCOC(=O)CNC(=O)Nc1nc2ccccc2n1C]

yield: 38%
mp: 157° C.
$^1$H NMR (300 MHz, CDCl$_3$) δ 7.10-7.17 (m, 4H, Ar—H), 4.19-4.26 (q, 2H, $^2J$=7.2 Hz, $^3J$=14.4 Hz, ethyl-CH$_2$), 4.07 (d, 2H, J=5.4 Hz, CH$_2$), 3.54 (s, 3H, N—CH$_3$), 1.29 (t, 3H, $^2J$=7.5 Hz, $^3J$=14.4 Hz, ethyl-CH$_3$).

KHG26030

Synthesis of ethyl 3-(3-(1-methyl-1H-benzo[d]imidazole-2-yl)ureido)propanoate

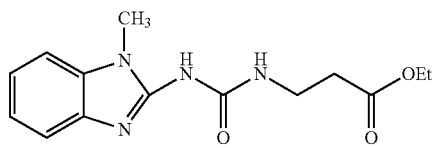 [SMILES: CCOC(=O)CCNC(=O)Nc1nc2ccccc2n1C]

yield: 8%
mp: 105° C.
$^1$H NMR (300 MHz, CDCl$_3$) δ 7.12-7.23 (m, 4H, Ar—H), 4.13-4.20 (q, 2H, $^2J$=6.9 Hz, $^3J$=14.1 Hz, ethyl-CH$_2$), 3.58-3.69 (d, 2H, J=7.5 Hz, CH$_2$), 3.54 (s, 3H, N—CH$_3$), 2.59-2.63 (t, 2H, $^2J$=5.7 Hz, $^3J$=12.0 Hz, CH$_2$), 1.27 (t, 3H, $^2J$=7.5 Hz, $^3J$=14.4 Hz, ethyl-CH$_3$).

KHG26031

Synthesis of ethyl 4-(3-(1-methyl-1H-benzo[d]imidazole-2-yl)ureido)butanoate

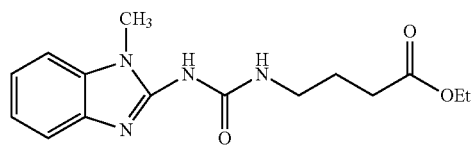 [SMILES: CCOC(=O)CCCNC(=O)Nc1nc2ccccc2n1C]

yield: 8° A
mp: 81° C.
$^1$H NMR (300 MHz, CDCl$_3$) δ 7.12-7.23 (m, 4H, Ar—H), 4.13-4.20 (q, 2H, $^2J$=6.9 Hz, $^3J$=14.1 Hz, OCH$_2$CH$_3$), 3.58-3.69 (d, 2H, J=7.5 Hz, CH$_2$), 3.54 (s, 3H, N—CH$_3$), 2.59-2.63 (t, 2H, $^2J$=5.7 Hz, $^3J$=12.0 Hz, CH$_2$), 1.27 (t, 3H, $^2J$=7.5 Hz, $^3J$=14.4 Hz, OCH$_2$CH$_3$).

KHG26096

Synthesis of potassium 2-(3-benzo[d]thiazole-2-ylureido)acetate

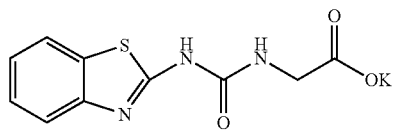

yield: 86.7%
mp: 234° C.
$^1$H NMR (300 MHz, D$_2$O) δ 7.75-7.20 (m, 4H, Ar—H), 3.70 (s, 2H, CH$_2$).

KHG26172

Synthesis of potassium 2-(3-(1-methyl-1H-benzo[d]imidazole-2-yl)ureido)acetate

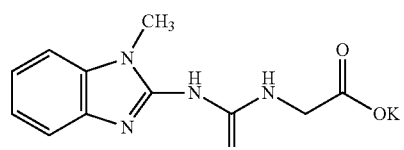

yield: 76.61%
mp: 229° C.
$^1$H NMR (300 MHz, D$_2$O) δ 7.20-7.07 (m, 4H, Ar—H), 3.60 (s, 2H, CH$_2$), 3.36 (s, 3H, CH$_3$).

KHG26175

Synthesis of potassium 2-(3-(6-methoxybenzo[d]thiazole-2-yl)ureido)acetate

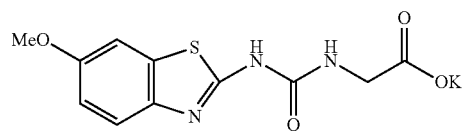

yield: 71.38%
mp: 264° C.
$^1$H NMR (300 MHz, D$_2$O) δ 7.34-6.83 (m, 3H, Ar—H), 3.70 (d, 3H, $^4J$=1.5 Hz, OCH$_3$), 3.67 (d, 2H, $^3J$=1.8 Hz, CH$_2$).

KHG26176

Synthesis of potassium 2-(3-(6-methoxybenzo[d]thiazole-2-yl)ureido)acetate

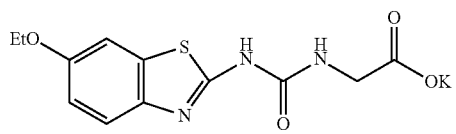

yield: 44% mp: 246° C.

$^1$H NMR (300 MHz, D$_2$O) δ 7.40-6.88 (m, 3H, Ar—H), 4.00 (q, 2H, $^3$J=6.9 Hz, OCH$_2$CH$_3$), 3.77 (s, 2H, CH$_2$), 1.35 (t, 3H, $^3$J=6.9 Hz, OCH$_2$CH$_3$).

KHG26177

Synthesis of potassium 2-(3-(6-chlorobenzo[d]thiazole-2-yl)ureido)acetate

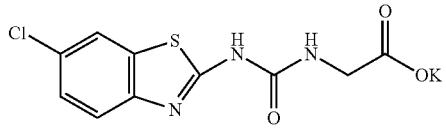

yield: 24% mp: 237° C.

$^1$H NMR (300 MHz, D$_2$O) δ 7.61-7.26 (m, 3H, Ar—H), 3.76 (s, 2H, CH$_2$).

KHG26178

Synthesis of potassium 2-(3-(4-chlorobenzo[d]thiazole-2-yl)ureido)acetate

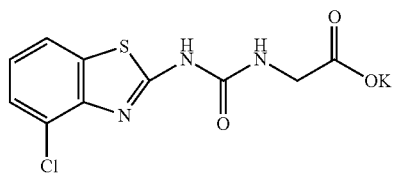

yield: 50% mp: 259° C.

$^1$H NMR (300 MHz, D$_2$O) δ 7.57-7.07 (m, 3H, Ar—H), 3.74 (s, 2H, CH$_2$).

KHG26180

Synthesis of potassium 2-(3-(5,6-dimethylbenzo[d]thiazole-2-yl)ureido)acetate

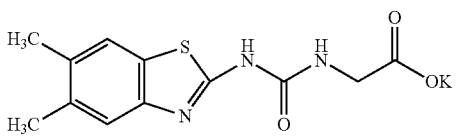

yield: 92.5% mp: 278° C.

$^1$H NMR (300 MHz, D$_2$O) δ 7.34 (m, 2H, Ar—H), 3.74 (s, 2H, CH$_2$), 2.24 (d, 6H, $^5$J=4.5 Hz, 2×CH$_3$).

KHG26216

Synthesis of potassium 2-(3-(6-methylbenzo[d]thiazole-2-yl)ureido)acetate

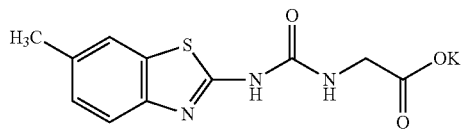

yield: 48.2% mp: 236° C.

$^1$H NMR (300 MHz, D$_2$O) δ 7.07-7.37 (m, 3H, Ar—H), 3.64 (s, 2H, CH$_2$), 2.26 (s, 3H, CH$_3$).

KHG26217

Synthesis of potassium 2-(3-(4-methylbenzo[d]thiazole-2-yl)ureido)acetate

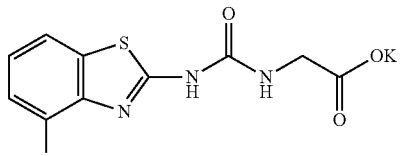

yield: 56.1% mp: 264.4° C.

$^1$H NMR (300 MHz, D$_2$O) δ 7.07-7.54 (m, 3H, Ar—H), 3.69 (s, 2H, CH$_2$), 2.41 (s, 3H, CH$_3$).

KHG26220

Synthesis of potassium 3-(3-benzo[d]thiazole-2-ylureido)propanoate

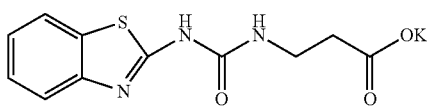

yield: 54.9% mp: 249° C.

$^1$H NMR (300 MHz, D$_2$O) δ 7.19-7.73 (m, 4H, Ar—H), 3.35 (t, $^3$J=6.7 Hz, 2H, CH$_2$), 2.37 (t, $^3$J=6.7 Hz, 3H, CH$_2$).

KHG26221

Synthesis of potassium 4-(3-benzo[d]thiazole-2-ylureido)butanoate

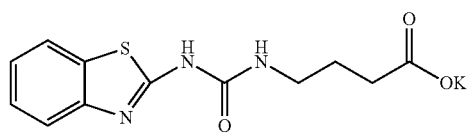

yield: 63.8% mp: 241° C.

$^1$H NMR (300 MHz, D$_2$O) δ 7.66-7.15 (m, 4H, Ar—H), 3.11 (t, 2H, $^3$J=6.9 Hz, CH$_2$CH$_2$CH$_2$), 2.21 (t, 3H, $^3$J=7.2 Hz, CH$_2$CH$_2$CH$_2$), 1.74 (q, 2H, $^3$J=7.5 Hz, CH$_2$CH$_2$CH$_2$).

KHG26222

Synthesis of potassium 3-(3-(1-methyl-1H-benzo[d]imidazole-2-yl)ureido)propanoate

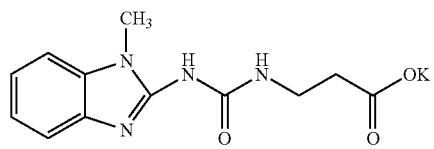

yield: 5.5% mp: 219° C.

$^1$H NMR (300 MHz, D$_2$O) δ 7.21-7.14 (m, 4H, Ar—H), 3.42 (t, 2H, $^3$J=6.6 Hz, CH$_2$CH$_2$), 3.3 (s, 3H, N—CH$_3$), 2.45 (t, 2H, $^3$J=7.2, CH$_2$CH$_2$).

KHG26223

Synthesis of potassium 3-(3-(1-methyl-1H-benzo[d]imidazole-2-yl)ureido)propanoate

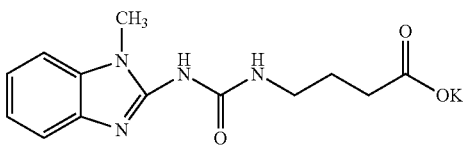

yield: 57.1% mp: 222° C.

$^1$H NMR (300 MHz, D$_2$O) δ 7.04-7.40 (m, 4H, Ar—H), 3.57 (s, 3H, CH$_3$), 3.13 (q, $^3$J=6.1 Hz, 2H, N—CH$_2$CH$_2$CH$_2$), 1.89 (t, $^3$J=7.1 Hz, 2H, N—CH$_2$CH$_2$CH$_2$), 1.62 (q, $^3$J=6.9 Hz, 2H, N—CH$_2$CH$_2$CH$_2$).

KHG26279

Synthesis of 1-(benzo[d]thiazole-2-yl)-3-(2-hydroxyethyl)urea

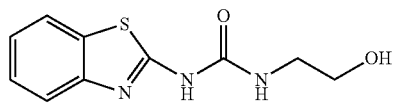 [SMILES: O=C(NCCO)Nc1nc2ccccc2s1]

yield: 27.2% mp: 223° C.

$^1$H NMR (300 MHz, DMSO-d$_6$) δ 10.65 (s, 1H, NH), 7.17-7.87 (m, 4H, Ar—H), 6.83 (brs, 1H, NH), 4.84 (q, $^3$J=5.1 Hz, 1H, OH), 3.47 (q, $^3$J=5.7 Hz, $^3$J=5.1 Hz, 2H, N—CH$_2$CH$_2$), 3.22 (q, $^3$J=5.7 Hz, 2H, CH$_2$CH$_2$OH).

KHG26280

Synthesis of 2-(3-(1-methyl-1H-benzo[d]imidazole-2-yl)ureido)acetic acid

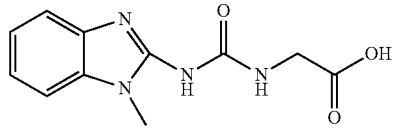 [SMILES: Cn1c(NC(=O)NCC(=O)O)nc2ccccc21]

yield: 91.8% mp: 200° C.

$^1$H NMR (300 MHz, DMSO-d$_6$) δ 7.28-7.63 (m, 4H, Ar—H), 3.91 (d, $^3$J=5.5 Hz, 2H, CH$_2$), 3.77 (s, 3H, CH$_3$).

KHG26303

Synthesis of ethyl 2-(3-(1-methyl-1H-benzo[d]imidazole-2-yl)thioureido)acetate

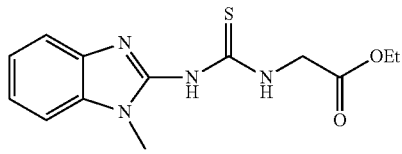 [SMILES: CCOC(=O)CNC(=S)Nc1nc2ccccc2n1C]

yield: 58.5% mp: 185° C.

¹H NMR (300 MHz, DMSO-d$_6$) δ 7.28-7.63 (m, 4H, Ar—H), 4.11 (q, 2H, ³J=7.2 Hz, OCH$_2$CH$_3$), 3.91 (d, ³J=5.5 Hz, 2H, CH$_2$), 3.32 (s, 3H, CH$_3$), 1.17 (t, ³J=7.2 Hz, 3H, OCH$_2$CH$_3$).

KHG26304

Synthesis of ethyl 2-(3-benzo[d]thiazole-2-ylthioureido)acetate

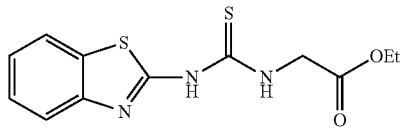 [SMILES: CCOC(=O)CNC(=S)Nc1nc2ccccc2s1]

yield: 18.5% mp: 204° C.

¹H NMR (300 MHz, DMSO-d$_6$) δ 7.26-7.92 (m, 4H, Ar—H), 4.40 (brs, 2H, CH$_2$), 4.15 (q, ³J=7.2 Hz, 2H, OCH$_2$CH$_3$), 1.22 (t, ³J=7.2 Hz, 3H, OCH$_2$CH$_3$).

KHG26305

Synthesis of ethyl 2-(3-(6-methylbenzo[d]thiazole-2-yl)thioureido)acetate

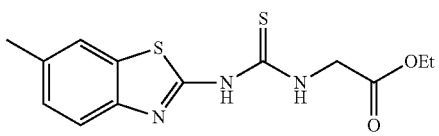 [SMILES: CCOC(=O)CNC(=S)Nc1nc2ccc(C)cc2s1]

yield: 40% mp: 290.8° C.

¹H NMR (300 MHz, DMSO-d$_6$) δ 7.57-7.12 (m, 3H, Ar—H), 4.30 (d, 2H, ³J=5.1 Hz, CH$_2$), 4.24 (q, 2H, ³J=7.2 Hz, OCH$_2$CH$_3$), 2.33 (s, 3H, CH$_3$), 1.29 (t, 3H, ³J=6.9 Hz, OCH$_2$CH$_3$).

KHG26306

Synthesis of ethyl 2-(3-(4-methylbenzo[d]thiazole-2-yl)thioureido)acetate

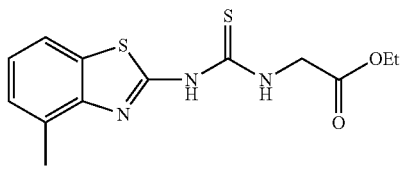 [SMILES: CCOC(=O)CNC(=S)Nc1nc2c(C)cccc2s1]

yield: 10.0% mp: 219° C.

¹H NMR (300 MHz, DMSO-d$_6$) δ 7.59-7.02 (m, 3H, Ar—H), 4.43 (d, 2H, ³J=5.1 Hz, CH$_2$), 4.17 (q, 2H, ³J=7.2 Hz, OCH$_2$CH$_3$), 2.42 (s, 3H, CH$_3$), 1.23 (t, 3H, ³J=7.2 Hz, OCH$_2$CH$_3$)

KHG26307

Synthesis of ethyl 2-(3-(5,6-dimethylbenzo[d]thiazole-2-yl)thioureido)acetate

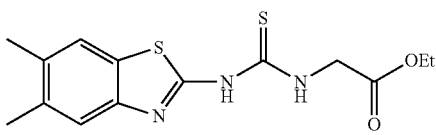 [SMILES: CCOC(=O)CNC(=S)Nc1nc2cc(C)c(C)cc2s1]

yield: 32.5% mp: 255° C.

¹H NMR (300 MHz, DMSO-d$_6$) δ 7.12-7.65 (m, 2H, Ar—H), 4.39 (brs, 2H, CH$_2$), 4.15 (q, ³J=6.9 Hz, 2H, OCH$_2$CH$_3$), 2.29 (d, ⁴J=4.5 Hz, 2|λCH$_3$), 1.22 (t, ³J=6.9 Hz, 3H, OCH$_2$CH$_3$).

KHG26308

Synthesis of ethyl 2-(3-(6-methoxybenzo[d]thiazole-2-yl)thioureido)acetate

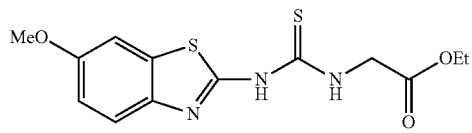 [SMILES: CCOC(=O)CNC(=S)Nc1nc2ccc(OC)cc2s1]

yield: 23.2% mp: 324° C.

¹H NMR (300 MHz, DMSO-d$_6$) δ 7.29-6.78 (m, 3H, Ar—H), 4.31 (d, 2H, ³J=4.8 Hz, CH$_2$), 4.24 (q, 2H, ³J=7.2 Hz, OCH$_2$CH$_3$), 3.72 (s, 3H, OCH$_3$), 1.31 (t, 3H, ₃J=7.2 Hz, OCH$_2$CH$_3$).

KHG26309

Synthesis of ethyl 2-(3-(6-ethoxybenzo[d]thiazole-2-yl)thioureido)acetate

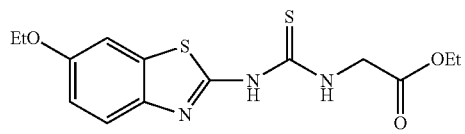 [SMILES: CCOC(=O)CNC(=S)Nc1nc2ccc(OCC)cc2s1]

yield: 26.0% mp: 183° C.

$^1$H NMR (300 MHz, DMSO-d$_6$) δ 7.12-7.65 (m, 2H, Ar—H), 4.39 (brs, 2H, CH$_2$), 4.15 (q, $^3$J=6.9 Hz, 2H, OCH$_2$CH$_3$), 1.22 (t, $^3$J=6.9 Hz, 3H, OCH$_2$CH$_3$).

KHG26310

Synthesis of ethyl 2-(3-(6-fluorobenzo[d]thiazole-2-yl)thioureido)acetate

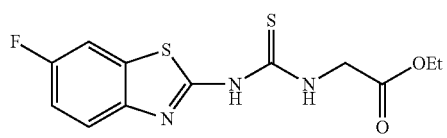 [SMILES: CCOC(=O)CNC(=S)Nc1nc2ccc(F)cc2s1]

yield: 5.4% mp: 160° C.

$^1$H NMR (300 MHz, DMSO-d$_6$) δ 7.59-6.99 (m, 3H, Ar—H), 4.39 (brs, 2H, CH$_2$), 4.15 (q, $^3$J=6.9 Hz, 2H, OCH$_2$CH$_3$), 1.22 (t, $^3$J=6.9 Hz, 3H, OCH$_2$CH$_3$).

KHG26311

Synthesis of ethyl 2-(3-(6-chlorobenzo[d]thiazole-2-yl)thioureido)acetate

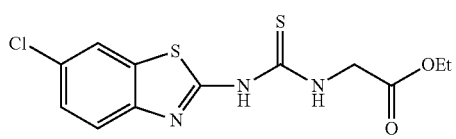 [SMILES: CCOC(=O)CNC(=S)Nc1nc2ccc(Cl)cc2s1]

yield: 15.2% mp: 184° C.

$^1$H NMR (300 MHz, DMSO-d$_6$) δ 7.77-7.19 (m, 3H, Ar—H), 4.31 (d, 2H, $^3$J=4.8 Hz, CH$_2$), 4.24 (q, $^3$J=6.9 Hz, 2H, OCH$_2$CH$_3$), 1.29 (t, $^3$J=7.2 Hz, 3H, OCH$_2$CH$_3$).

KHG26312

Synthesis of ethyl 2-(3-(4-chlorobenzo[d]thiazole-2-yl)thioureido)acetate

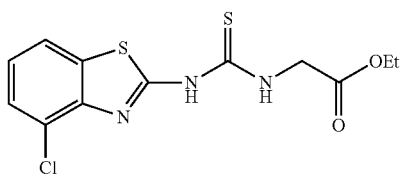 [SMILES: CCOC(=O)CNC(=S)Nc1nc2c(Cl)cccc2s1]

yield: 12.3% mp: 198° C.

$^1$H NMR (300 MHz, DMSO-d$_6$) δ 7.83-6.96 (m, 3H, Ar—H), 4.31 (d, 2H, $^3$J=4.8 Hz, CH$_2$), 4.24 (q, $^3$J=6.9 Hz, 2H, OCH$_2$CH$_3$), 1.29 (t, $^3$J=7.2 Hz, 3H, OCH$_2$CH$_3$).

KHG26316

Synthesis of 2-(3-benzo[d]thiazole-2-ylthioureido)acetic acid

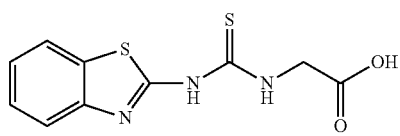 [SMILES: O=C(O)CNC(=S)Nc1nc2ccccc2s1]

yield: 93.3% mp 200° C.

$^1$H NMR (300 MHz, DMSO-d$_6$) δ 10.05 (brs, 1H, NH), 7.97-7.18 (m, 4H, Ar—H), 4.32 (d, 2H, $^3$J=5.4 Hz, CH$_2$).

KHG26332

Synthesis of 1-(benzo[d]thiazole-2-yl)-3-ethylurea

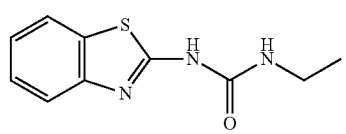

yield: 73% mp: 197° C.

$^1$H NMR (300 MHz, DMSO-d$_6$) δ 10.66 (brs, 1H, NH), 7.87-7.17 (m, 4H, Ar—H), 6.71 (t, 1H, J=8.7 Hz, NH), 3.23-3.14 (m, 2H, ethyl CH$_2$), 1.08 (t, 3H, J=7.2 Hz, CH$_3$).

KHG26334

Synthesis of 2-(3-(1-methyl-1H-benzo[d]imidazole-2-yl)thioureido)acetic acid

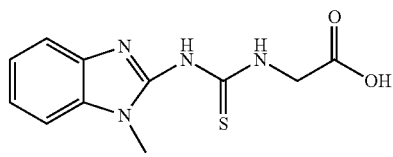 [SMILES: Cn1c(NC(=S)NCC(=O)O)nc2ccccc21]

yield: 67%
mp: 172° C.
$^1$H NMR (300 MHz, DMSO-d$_6$) δ 13.24 (brs, 1H, NH), 8.11 (brs, 1H, NH), 7.63-7.18 (m, 4H, Ar—H), 3.92 (d, 2H, $^3$J=6.0 Hz, CH$_2$), 3.52 (s, 3H, CH$_3$).

KHG26335

Synthesis of 2-(3-(5,6-dimethylbenzo[d]thiazole-2-yl)thioureido)acetic acid

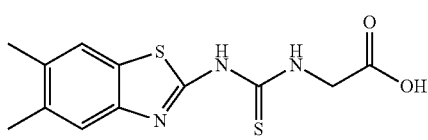 [SMILES: Cc1cc2nc(NC(=S)NCC(=O)O)sc2cc1C]

yield: 91%
mp: 212° C.
$^1$H NMR (300 MHz, DMSO-d$_6$) δ 7.65-7.43 (m, 2H, Ar—H), 4.32 (d, 2H, $^3$J=5.1 Hz, CH$_2$), 2.30 (d, 6H, $^3$J=3.9 Hz, 2[λCH$_3$).

KHG26336

Synthesis of 2-(3-(6-ethoxybenzo[d]thiazole-2-yl)thioureido)acetic acid

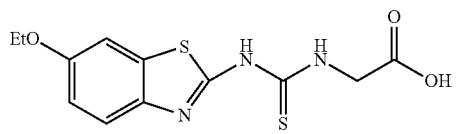 [SMILES: CCOc1ccc2nc(NC(=S)NCC(=O)O)sc2c1]

yield: 24%
mp: 200° C.
$^1$H NMR (300 MHz, DMSO-d$_6$) δ 7.55-6.98 (m, 3H, Ar—H), 4.34 (d, 2H, 3J=Hz, CH$_2$), 4.05 (q, 2H, $^3$J=7.2 Hz, OCH$_2$CH$_3$), 1.34 (t, 3H, $^3$J=6.9 Hz, OCH$_2$CH$_3$).

KHG26340

Synthesis of 2-(3-(4-methylbenzo[d]thiazole-2-yl)thioureido)acetic acid

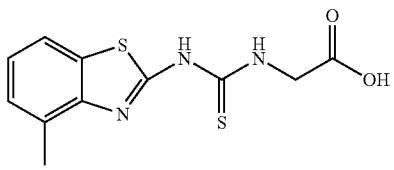 [SMILES: Cc1cccc2sc(NC(=S)NCC(=O)O)nc12]

yield: 60%
mp: 214° C.
$^1$H NMR (300 MHz, DMSO-d$_6$) δ 7.75-7.16 (m, 3H, Ar—H), 4.34 (d, 2H, $^3$J=4.8 Hz, CH$_2$), 2.58 (s, 3H, CH$_3$).

KHG26341

Synthesis of 2-(3-(6-chlorobenzo[d]thiazole-2-yl)thioureido)acetic acid

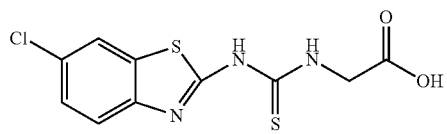 [SMILES: O=C(O)CNC(=S)Nc1nc2ccc(Cl)cc2s1]

yield: 38%
mp: 193° C.
$^1$H NMR (300 MHz, DMSO-d$_6$) δ 8.06-7.42 (m, 3H, Ar—H), 4.31 (d, 2H, $^3$J=5.4 Hz, CH$_2$).

KHG26342

Synthesis of N-(benzo[d]thiazole-2-yl)-2-cyanoacetamide

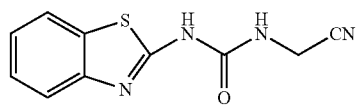 [SMILES: N#CCNC(=O)Nc1nc2ccccc2s1]

yield: 54%
mp: 143° C.
$^1$H NMR (300 MHz, DMSO-d$_6$) δ 11.43 (brs, 1H, NH), 7.91-7.20 (m, 4H, Ar—H), 7.44 (t, 1H, $^3$J=5.4 Hz, NH), 4.23 (d, 2H, $^3$J=5.7 Hz, CH$_2$).

KHG26344

Synthesis of 1-(benzo[d]thiazole-2-yl)-3-(2-methoxyethyl)urea

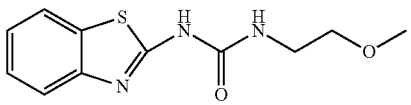 [SMILES: COCCNC(=O)Nc1nc2ccccc2s1]

yield: 80%
mp: 257° C.
$^1$H NMR (300 MHz, DMSO-$d_6$) δ 10.62 (brs, 1H, NH), 7.89-7.19 (m, 4H, Ar—H), 6.86 (brs, 1H, NH), 3.43 (q, 2H, $^3$J=5.1 Hz, CH$_2$CH$_2$), 3.30 (s, 3H, OCH$_3$), 3.2 (brs 2H, CH$_2$CH$_2$).

KHG26345

Synthesis of N-(benzo[d]thiazole-2-yl)-2-(2H-tetrazole-5-yl)acetamide

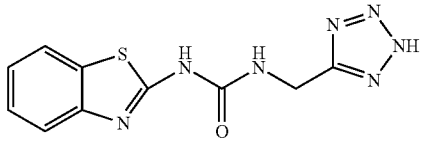 [SMILES: O=C(NCc1nn[nH]n1)Nc1nc2ccccc2s1]

yield: 20%
mp: 249° C.
$^1$H NMR (300 MHz, DMSO-$d_6$) δ 8.30-7.19 (m, 4H, Ar—H), 7.04 (t, 1H, $^3$J=6.6 Hz, NH), 3.89 (d, 2H, $^3$J=5.7 Hz, CH$_2$).

KHG26346

Synthesis of 2-(3-(6-methoxybenzo[d]thiazole-2-yl)ureido)acetic acid

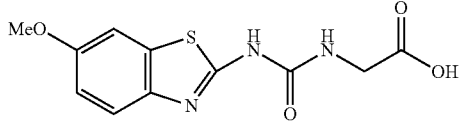 [SMILES: COc1ccc2nc(NC(=O)NCC(=O)O)sc2c1]

yield: 95%
mp: 198.3° C.
$^1$H NMR (300 MHz, DMSO-$d_6$) δ 7.53-6.93 (m, 3H, Ar—H), 6.98 (brs, 1H, NH), 3.87 (d, 2H, $^3$J=5.7 Hz, CH$_2$), 3.78 (s, 3H, OCH$_3$).

KHG26347

Synthesis of ethyl 2-(3-(6-ethoxybenzo[d]thiazole-2-yl)ureido)acetate

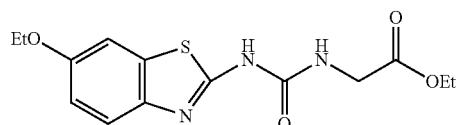

yield: 81%
mp: 264° C.
$^1$H NMR (300 MHz, DMSO-$d_6$) δ 10.85 (s, 1H, NH), 7.52-6.92 (m, 3H, Ar—H), 7.03 (brs, 1H, NH), 4.13 (q, 2H, $^3$J=7.2 Hz, OCH$_2$CH$_3$), 4.03 (q, 2H, $^3$J=6.9 Hz, OCH$_2$CH$_3$), 3.95 (d, 2H, $^3$J=5.7 Hz, CH$_2$) 1.33 (t, 3H, $^3$J=6.9 Hz, OCH$_2$CH$_3$) 1.21 (t, 3H, $^3$J=7.2 Hz, OCH$_2$CH$_3$).

KHG26348

Synthesis of 2-(3-(6-ethoxybenzo[d]thiazole-2-yl)ureido)acetic acid

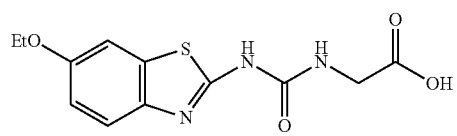 [SMILES: CCOC(=O)CNC(=O)Nc1nc2ccc(OCC)cc2s1]

yield: 97%
mp: 197° C.
$^1$H NMR (300 MHz, DMSO-$d_6$) δ 7.52-6.92 (m, 3H, Ar—H), 6.98 (t, 1H, $^3$J=5.7 Hz, NH), 4.03 (q, 2H, $^3$J=6.9 Hz, OCH$_2$CH$_3$), 3.88 (d, 2H, $^3$J=5.7 Hz, CH$_2$) 1.33 (t, 3H, $^3$J=6.9 Hz, OCH$_2$CH$_3$).

KHG26349

Synthesis of ethyl 2-(3-(6-chlorobenzo[d]thiazole-2-yl)ureido)acetate

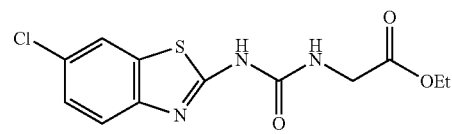 [SMILES: CCOC(=O)CNC(=O)Nc1nc2ccc(Cl)cc2s1]

yield: 93%
mp 295° C.
$^1$H NMR (300 MHz, DMSO-$d_6$) δ 11.15 (s, 1H, NH), 8.02-7.36 (m, 3H, Ar—H), 7.08 (brs, 1H, NH), 4.13 (q, 2H, $^3$J=7.2 Hz, OCH$_2$CH$_3$), 3.96 (d, 2H, $^3$J=5.7 Hz, CH$_2$), 1.21 (t, 3H, $^3$J=6.9 Hz, OCH$_2$CH$_3$).

KHG26350

Synthesis of 2-(3-(6-chlorobenzo[d]thiazole-2-yl)ureido)acetic acid

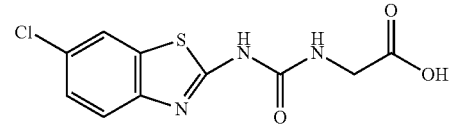 [SMILES: O=C(O)CNC(=O)Nc1nc2ccc(Cl)cc2s1]

yield: 87%
mp: 216° C.
$^1$H NMR (300 MHz, DMSO-$d_6$) δ 8.02-7.35 (m, 3H, Ar—H), 7.01 (t, 1H, $^3$J=5.4 Hz, NH), 3.89 (d, 2H, $^3$J=5.7 Hz, CH$_2$).

29
KHG26351

Synthesis of ethyl 2-(3-(4-chlorobenzo[d]thiazole-2-yl)ureido)acetate

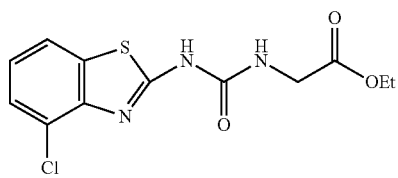 [SMILES: CCOC(=O)CNC(=O)Nc1nc2c(Cl)cccc2s1]

yield: 96%
mp: 213° C.
¹H NMR (300 MHz, DMSO-d₆) δ 11.59 (s, 1H, NH), 7.88-7.18 (m, 3H, Ar—H), 6.91 (brs, 1H, NH), 4.13 (q, 2H, 3J=7.2 Hz, OCH₂CH₃), 3.95 (d, 2H, ³J=5.4 Hz, CH₂), 1.21 (t, 3H, ³J=6.9 Hz, OCH₂CH₃).

KHG26352

Synthesis of 2-(3-(4-chlorobenzo[d]thiazole-2-yl)ureido)acetic acid

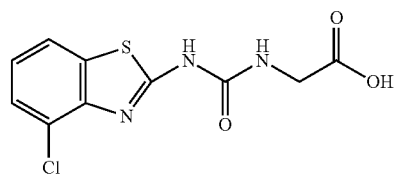 [SMILES: O=C(O)CNC(=O)Nc1nc2c(Cl)cccc2s1]

yield: 98%
mp: 198° C.
¹H NMR (300 MHz, DMSO-d₆) δ 11.52 (s, 1H, NH), 7.89-7.18 (m, 3H, Ar—H), 6.85 (brs, 1H, NH), 3.88 (d, 2H, ³J=5.4 Hz, CH₂).

KHG26353

Synthesis of ethyl 2-(3-(5,6-dimethylbenzo[d]thiazole-2-yl)ureido)acetate

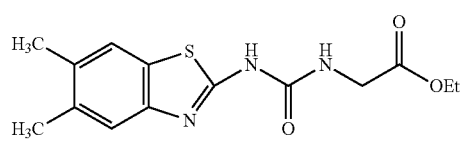 [SMILES: CCOC(=O)CNC(=O)Nc1nc2cc(C)c(C)cc2s1]

yield: 97%
mp: 268° C.
¹H NMR (300 MHz, DMSO-d₆) δ

30
KHG26354

Synthesis of 2-(3-(5,6-dimethylbenzo[d]thiazole-2-yl)ureido)acetic acid

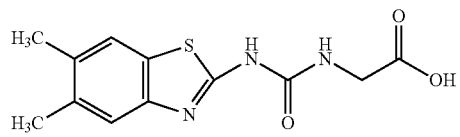

yield: 89%
mp: 198° C.
¹H NMR (300 MHz, DMSO-d₆) δ 7.61-7.41 (m, 2H, Ar—H), 7.03 (brs, 1H, NH), 3.87 (d, 2H, ³J=5.4 Hz, CH₂), 2.27 (d, 6H, ³J=2.7 Hz, 2[λCH₃).

KHG26355

Synthesis of 2-(3-(6-methylbenzo[d]thiazole-2-yl)ureido)acetic acid

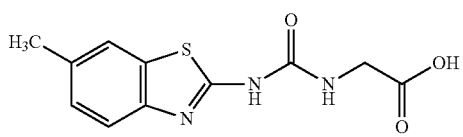

yield: 90%
mp: 201° C.
¹H NMR (300 MHz, DMSO-d₆) δ 7.66-7.15 (m, 3H, Ar—H), 7.05 (t, 1H, ³J=5.4 Hz, NH), 3.88 (d, 2H, ³J=5.7 Hz, CH₂), 2.37 (s, 3H, CH₃).

KHG26356

Synthesis of 2-(3-(4-methylbenzo[d]thiazole-2-yl)ureido)acetic acid

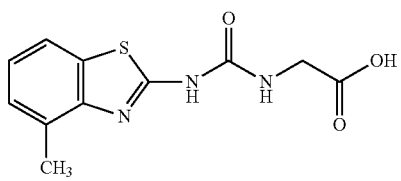

yield: 96%
mp: 203° C.
¹H NMR (300 MHz, DMSO-d₆) δ 7.69-7.08 (m, 3H, NH), 6.92 (brs, 1H, NH), 3.88 (d, 2H, ³J=5.6 Hz, CH₂), 2.52 (s, 3H, CH₃).

KHG26357

Synthesis of 3-(3-(1-methyl-1H-benzo[d]imidazole-2-yl)ureido)propane acid

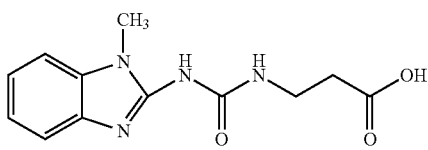 [SMILES: Cn1c(NC(=O)NCCC(=O)O)nc2ccccc21]

yield: 37.5%
mp: 237° C.
$^1$H NMR (300 MHz, DMSO-$d_6$) δ 12.35 (brs, 1H, NH), 7.54-7.26 (m, 4H, Ar—H), 3.73 (s, 3H, CH$_3$), 3.42 (q, 2H, $^3$J=6.0 Hz, CH$_2$), 2.50 (brs, 2H, CH$_2$).

KHG26358

Synthesis of 4-(3-(1-methyl-1H-benzo[d]imidazole-2-yl)ureido)butanoic acid

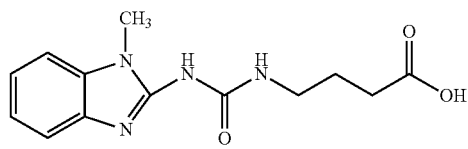 [SMILES: Cn1c(NC(=O)NCCCC(=O)O)nc2ccccc21]

yield: 52%
mp: 197° C.
$^1$H NMR (300 MHz, DMSO-$d_6$) δ 7.36-7.11 (m, 4H, Ar—H), 3.64 (brs, 2H, CH$_2$CH$_2$CH$_2$), 3.33 (s, 3H, N—CH$_3$), 2.27 (t, 2H, $^3$J=6.6 Hz, CH$_2$CH$_2$CH$_2$), 1.72 (m, 2H, CH$_2$CH$_2$CH$_2$).

Experimental Example 1

Treatment of Beta-Amyloid

Beta-amyloid (Aβ$_{25-35}$, Sigma Chemical Co., St. Louis, Mo., USA) was diluted with aseptic desalted water and preservative solution (1 mM, GIBCO), and kept in aliquots at −70° C. To the treatment of beta-amyloid, beta-amyloid preservative solution was diluted to desired concentrations in a treatment medium (DMEM, GIBCO). The reagents were newly provided as a preservative solution (10 mM) under DMSO (dimethylsulfoxide), and diluted in treatment medium to desired concentrations.

Cell Culture

BV-2 microglia cells (allotted from Pharmacology Division of Ajou University) were cultivated in DMEM (Dulbecco's Modified Eagle's Medium) supplemented with 5% fetal bovine serum (Invitrogen, Carlsbad, Calif., USA), sou/Ml penicillin (Invitrogen, Carlsbad, Calif., USA), and 50 μg/Ml streptomycin (Invitrogen, Carlsbad, Calif., USA) under the atmosphere condition with 5% CO$_2$ and 95% air at 37° C. The medium was replaced once a day, the cells were plate-cultured in a density according to the scale of each experiment.

Measurement of Cell Viability (Cell Survival Rate)

BV-2 cells were plate-cultured in 96-well plate at the density of 5×10$^4$, the cell viability was measured according to a conventional MTT analysis method and lactate dehydrogenase (LDH) analysis method. The MTT analysis depends on the metabolism ability of mitochondria of living cell, and reflexes intracellular redox states. The cultured cells were treated with MTT a solution (final concentration: 1 mg/Ml) for 4 hours. Deep blue formazan crystal generated in the original cells was dissolved in a lysis buffer, and then, the absorbance was detected at 595 nm with microplate reader. The LDH activity released from the culture medium was detected, which was evaluated as a cell death index. The culture medium was added to a reagent (test, Sigma Chemical Co, St. Louis, Mo., USA) containing sodium lactate, NADH and sodium pyruvate, and then, the absorbance reduction by NADH at 340 nm was measured. The result was calculated assuming that the LDH activity in homogenate solution of the non-treated control is 100%.

Measurement of Cytokine

Lipopolysaccharide (LPS)-treated cells (6-well of 5×10$^5$ cells/3 Ml, Fluka, Sigma-Aldrich, St. Louis, Mo., USA) were collected, and washed with phosphate-buffered saline (PBS). The cells were centrifuged, and then dissolved in pro-prep lysis buffer at 4° C. Interleukin-1 beta and tumor necrosis factor-alpha in the cell lysis solution wherein the cells were dissolved were measured by enzyme-linked immunosorbent analysis plate (R&D systems inc, Minneapolis, Minn., USA). The absorbance at 450 nm was measured using microplate reader. In addition, cytokine was measured using a cytokine measuring system (R&D systems inc, Minneapolis, Minn., USA).

Animal Experiment

The animal experiment was performed using C57BL/6 mice (20-25 kg, 12-14 weeks old, Harlan Sprague Dawley inc, Indianapolis, Ind., USA) by stereotaxis. The intracerebroventricular (ICV) injection was according to the intracerebroventricular injection system described in Craft et al., 2004b. The mice were grown in an accommodation for SPF (specific pathogen free) under 12 hours light/12 hours dark repeat, and supplied with water and feed as recommended by the accommodation for SPF. The study was reviewed and approved by the Institutional Animal Care and Use Committee (IACUC) of Asan Institute for Life Sciences, Asan Medical Center, which abides by the Institute of Laboratory Animal Resources (ILAR) guide.

Western Blot Analysis

The beta-amyloid treated cells (6-well of 5×10$^5$ cells/3 Ml, allotted from Pharmacology Division of Ajou University) were collected, and washed with phosphate-buffered saline (PBS). After centrifugation, the cells were dissolved in 0.1 ml of RIPA buffer (containing 150 mM NaCl, 1% NP-40, 0.5% sodium deoxycholate, 0.1% SDS, 50 mM Tris-HCl, pH 7.4, 50 mM glyycerophosphate, 20 mM NaF, 20 mM EGTA, 1 mM DTT, 1 mM Na$_3$VO$_4$, and protease inhibitor) at 4° C. for 15 minutes by strong shaking. The cells were cultivated in ice for 10 minutes, the lysate was centrifuged at 14,000 rpm for 5 minutes. 20 μg of a protein obtained from the cell lysate was heated, and then, electrophoresed on 12% polyacrylamide gel under reduction condition. The cells were incubated in blocking buffer (20 mM Tris, pH 7.4-buffer saline containing 0.1% tween 20 containing 5% lipid-free dried milk) for 1 hour, to suppress non-specific binding.

Primary antibodies (anti-ERK1, anti-ERK2, anti-phosphoric acid-ERK1, and anti-phosphoric acid-ERK2, Cell Signaling Technology Inc, Beverly, Mass., USA) were exposed on membrane for 90 minutes. After washing, blots were incubated with horseradish peroxidation enzyme-conjugated anti-mouse IgG diluted at 1:1,000 for 1 hour. A detection using a chemiluminescent substrate (Pierce) was performed for 1 minute according to manufacturer's instruction, and the obtained results were visualized with X-ray film.

Statistical Analysis

The change of cell viability was analyzed using ANOVA (analysis of variance), Student's t-test was conducted. The cases with the p-value of 0.05 or less were considered as statistically meaningful results.

Result and Discussion

1. Effect of KHG25967 on Cell Inflammation Induced by Beta-Amyloid in BV-2 Cell

BV-2 cells were pre-treated with 50 μM of beta-amyloid, and 50 nM of KHG25967 compound was added to the beta-amyloid treated cells for 24 hours. For microscope analysis, BV-2 cells were used in 6-well plate at the density of $5\times10^5$ cells/well, for MTT analysis, BV-2 cells were used in 96-well plate at the density of $5\times10^4$ cells/well.

Figure 1A:
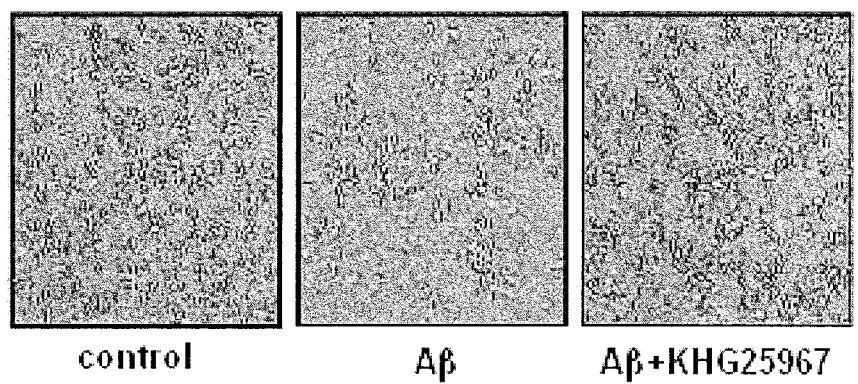
FIGS. 1A and 1B show the protecting activity of compound KHG25967 against neurotoxicity (Aβ25-35-induced cytotoxicity) of beta-amyloid in BV-2 cell compound KHG25967.
Figure 1B:
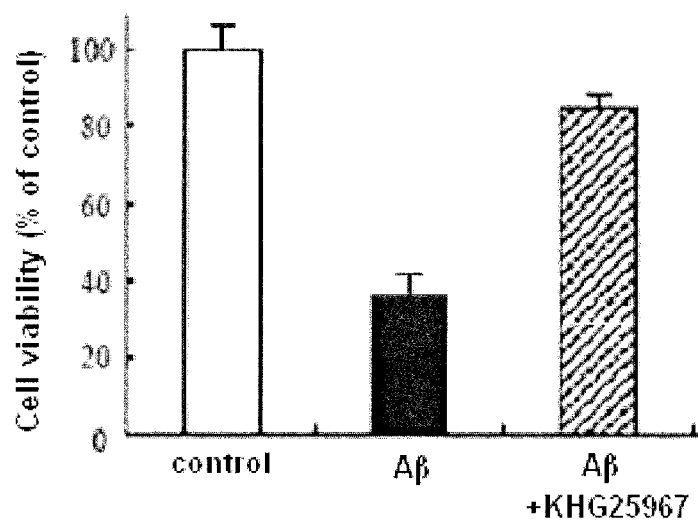

The obtained prevention effects of KHG25967 compound on toxicity induced by beta-amyloid in BV-2 cells were FIGS. 1A and 1b. FIG. 1A shows the shape of the cells observed by microscope analysis, 1B shows cell viability measured by MTT analysis. More specifically, FIG. 1A shows a control where both of beta-amyloid and KHG25967 were not treated, a case treated with 50 μM of beta-amyloid for 24 hours, and a case treated with 50 μM of beta-amyloid for 2 hours and then 50 nM KHG25967 for 24 hours, 1B shows the cell viabilities of each case shown in 1A.

As shown in FIG. 1A, compared to normal BV-2 cells (control), the beta-amyloid treated cells displays processes like nervous cells, are separated from the bottom, and exist in coagulated phase. The case treated with KHG25967, the morphological characteristics of damaged cells are alleviated.

In addition, as shown in FIG. 1B, the cell viability of beta-amyloid treated case (control) is 35%, and when KHG25967 is further treated, the cell viability increases to 83%, indicating that the cell viability can be considerably increased by the treatment of the compound of the present invention, KHG25967, compared with the control.

In nervous cell degeneration by beta-amyloid in BV-2 cells, the culture where KHG25967 was pre-treated prior to the addition of beta-amyloid shows a protective effect against nervous degeneration, which is similar to the case where KHG25967 was treated after the addition of beta-amyloid.

2. Effect of KHG25967 on the Activities of ERK1/2 and Caspase 3 Induced by Beta-Amyloid To examine the effect of compound KHG25967 on phosphorylation of ERK (extracellular signal-regulated kinase) and expression of caspase 3 by beta-amyloid, a possible protein expression of ERK1/2 (extracellular signal-regulated kinase 1 & 2) and caspase 3 in BV-2cell culture stimulated with beta-amyloid were measured.

Based on the fact that the activity of ERK depends on the phosphorylation of threonine and tyrosine, the measurement by immunoblotting analysiss using specific anti-phospho-ERK1/2 antibody and anti-ERK1/2 antibody (Cell Signaling Technology Inc, Beverly, Mass., USA) was performed.

The activity of caspase 3 was measured as a cleavage at aspartic acid and serine by a stimulation, which is measured using anti-cleavage-caspase 3 antibody (Cell Signaling Technology Inc, Beverly, Mass., USA) through immunoblotting analysis. Beta-actin (Sigma Chemical Co, St. Louis, Mo., USA) was used as a control for the measurement of a relative expression level.

Figure 2A:
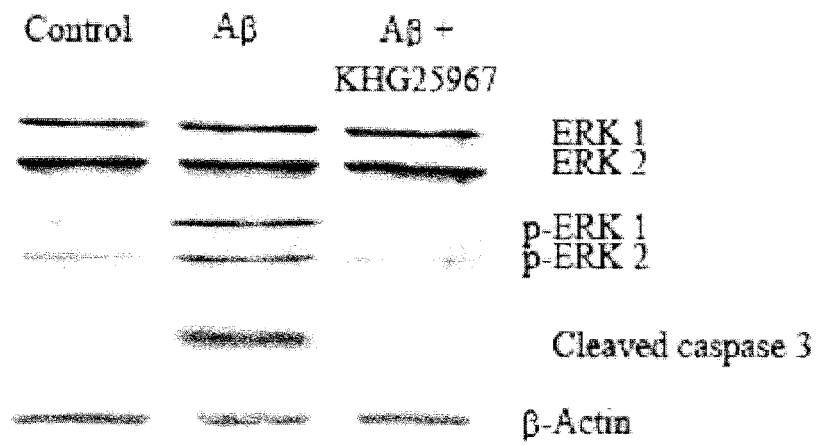
FIG. 2A to 2C show an effect of compound KHG25967 on phosphorylating activity of ERK1 and ERK2 and Caspase 3 activity.
Figure 2B:
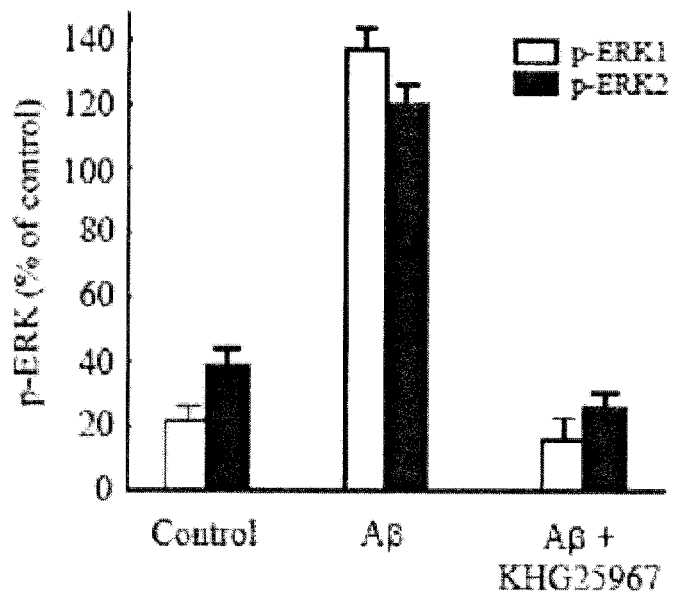
Figure 2C:
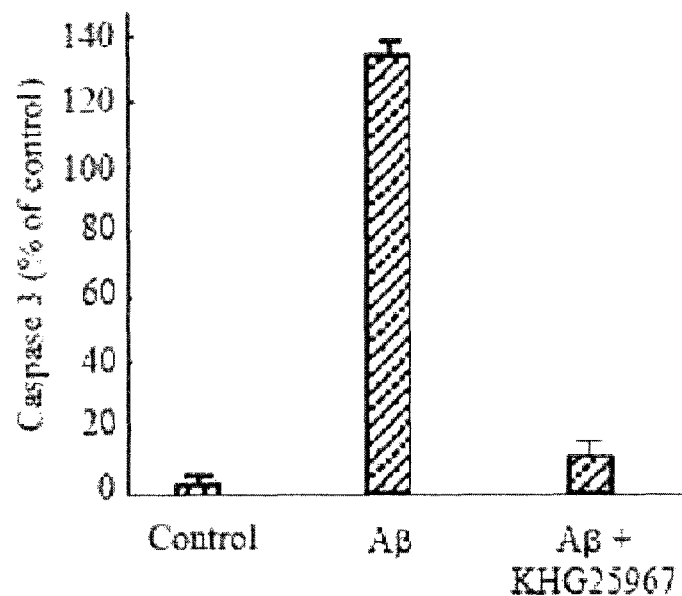

The obtained results are shown in FIGS. 2A to 2C. FIG. 2A shows the inhibition level of KHG25967 against caspase 3 and p-ERK induced by LPS in BV-2 cells using Western blot, revealing that in the culture treated with beta-amyloid in the presence of 50 nM KHG25967, the increase of phospho-ERK1/2 is considerably weakened.

In addition, FIG. 2B shows the inhibition level of KHG25967 against p-ERK induced by LPS in BV-2 cells by concentration measurement analysis, revealing that the culture treated with beta-amyloid together with KHG25967 shows reduced expression level of phospho-ERK1 and phospho-ERK2 by 90% and 70%, respectively, compared to those of the culture treated with beta-amyloid only.

In addition, FIG. 2C shows the inhibition level of KHG25967 against caspase 3 induced by LPS in BV-2 cells by concentration measurement analysis, revealing that the culture treated with beta-amyloid together with KHG25967 shows reduced expression level of cleavage-caspase 3 by 93%, compared to those of the culture treated with beta-amyloid only.

3. Effect of KHG25967 on the Change of Cytokine According to LPS-Induced Nervous Inflammation Change in BV-2 Cells BV-2 cells were pre-treated with 1 μg/ml of LPS (Fluka, Sigma-Aldrich, St. Louis, Mo., USA) for 2 hours, and then, further treated with 50 nM KHG25967 for 6 hours. The changed amounts of cytokines of tumor necrosis factor-alpha and interleukin-1beta were measured from lysate solution where the cells were dissolved in cell lysate solution (Intron Biotechnology, Seoul, Korea). The levels of cytokines of tumor necrosis factor-alpha and interleukin-1 beta are specifically increased in nervous cell inflammation reaction, and the level of specific cytokine can be measured by ELISA.

Figure 3A:
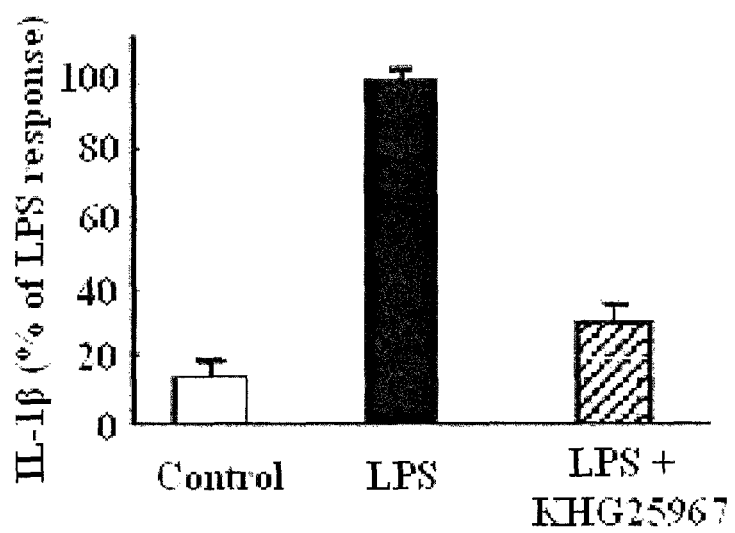
FIGS. 3A and 3B represent the in vivo protecting activity of compound KHG25967 against cytokine induced by LPS in BV-2 cell.
Figure 3B:
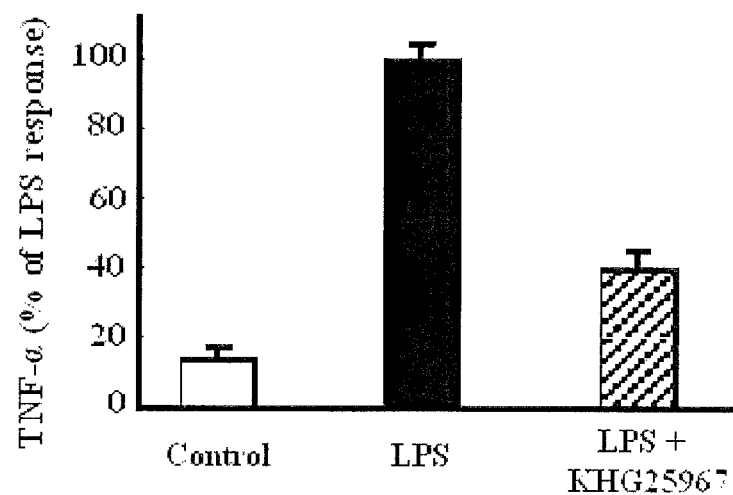

The inhibition effects of KHG25967 against the production of inflammatory cytokines, IL-1β and TNF-α, obtained from the BV-2 cell cultivation were shown in FIGS. 3A and 3b. As shown in FIGS. 3A and 3b, the levels of interleukin-1beta and tumor necrosis factor-alpha in the case treated with LPS and 50 nM KHG25967 are suppressed by 70% (interleukin-1beta) and 61% (tumor necrosis factor-alpha), respectively, compared to the level in the case treated with LPS only (assuming as 100%).

4. Brain Specific Effect of KHG25967 on the Change of Cytokines According to LPS-Induced Nervous Inflammation Change in C57BL/6 Mice Brain The effect of KHG25967 on the change of pro-inflammatory cytokines was examined in vivo using 12-14 week old C57BL/6 mice. The control group was administered with PBS only for 2 weeks and then, further treated with PBS for 6 hours. The LPS group was administered with PBS only for 2 weeks and then, 10 mg/kg of LPS was administered into brain using streotaxis. The KHG25967 treated group was administered with 10 mg/kg or 20 mg/kg of KHG25967 every day for 2 weeks, and then, 10 mg/kg of LPS was administered into brain using streotaxis. After 6 hours from LPS administration, blood (serum) was collected through heart or abdominal vein, and the brain was extracted and dissolved. The changes in the level of pro-inflammatory cytokines (interleukin-1beta and tumor necrosis factor-alpha) in the separated blood and brain were measured.

The selectivity results to inflammation of central nervous system by oral administration of KHG25967 were shown in FIGS. 4A to 4D. FIG. 4A shows the change in the level of interleukin-1beta in brain, 4B shows the change in the level of tumor necrosis factor-alpha in brain, 4C shows the change in the level of interleukin-1beta in serum, and 4D shows the change in the level of tumor necrosis factor-alpha in serum. As shown in FIGS. 4A and 4B, in the group administered with KHG25967 for 2 weeks and then with LPS, the levels of interleukin-1 beta and tumor necrosis factor-alpha in brain are decreased by 55% (interleukin-1beta) and 42% (tumor necrosis factor-alpha), respectively, compared with that in the group treated with LPS only (assuming as 100%).

In contrast, as shown in FIGS. 4 C and 4D, there is no specific difference in the levels of interleukin-1beta and tumor necrosis factor-alpha in blood regardless of KHG25967 administration. The results of the comparison between the changes in the levels of pro-inflammatory cytokines in peripheral blood and brain reveal that the effect of KHG25967 is specific to brain.

Experimental Example 2

Experiment of Viability (Cell Death Suppression)

BV-2 cells were pre-treated with 50 μM of beta-amyloid for 2 hours, and treated with each of the compounds shown in Table 2 for 24 hours. For MTT analysis, BV-2 cells were used on 96-well plate in the density of $5 \times 10^4$ cells/well. The quantitative analysis results (unit: %) for the cell viability obtained by MTT analysis were shown in Table 2, wherein the values are represented by the average of three experiments per each concentration.

TABLE 2

| Number of compound | 50 μM | 1000 nM | 500 nM | 100 nM | 50 nM |
|---|---|---|---|---|---|
| KHG25948 | 30 | | | | |
| KHG25954 | 48 | | | | |
| KHG25956 | 36 | | | | |
| KHG25967 | | | | | 83 |
| KHG25989 | 55 | | | | |
| KHG25990 | 37 | | | | |
| KHG26004 | 37 | | | | |
| KHG26005 | 40 | | | | |
| KHG26006 | 65 | | | | |
| KHG26019 | 47 | | | | |
| KHG26025 | 90 | 89 | | 73 | |
| KHG26026 | 82 | 85 | | 66 | |
| KHG26027 | 45 | | | | |
| KHG26028 | 34 | | | | |
| KHG26029 | 70 | 73 | | 86 | |
| KHG26030 | 75 | 76 | | 60 | |
| KHG26031 | 56 | | | | |
| KHG26096 | | | 72 | | |
| KHG26172 | | | 68 | | |
| KHG26175 | | | 76 | | |
| KHG26176 | | | 51 | | |
| KHG26177 | | | 62 | | |
| KHG26178 | | | 59 | | |
| KHG26180 | | | 62 | | |
| KHG26216 | | | 62 | | |
| KHG26217 | | | 49 | | |
| KHG26220 | | | 33 | | |
| KHG26221 | | | 44 | | |
| KHG26222 | | | 33 | | |
| KHG26223 | | | 51 | | |
| KHG26279 | | | 36 | | |
| KHG26280 | | | 33 | | |
| KHG26303 | | | 48 | | |
| KHG26304 | | | 41 | | |
| KHG26305 | | | 37 | | |
| KHG26306 | | | 62 | | |
| KHG26307 | | | 48 | | |
| KHG26308 | | | 44 | | |
| KHG26309 | | | 65 | | |
| KHG26310 | | | 30 | | |
| KHG26311 | | | 67 | | |
| KHG26312 | | | 55 | | |
| KHG26316 | | | 57 | | |
| KHG26332 | 18 | | | | |
| KHG26334 | | | 75 | | |
| KHG26335 | | | 81 | | |
| KHG26336 | | | 67 | | |
| KHG26340 | | | 78 | | |

TABLE 2-continued

| Number of compound | 50 μM | 1000 nM | 500 nM | 100 nM | 50 nM |
|---|---|---|---|---|---|
| KHG26341 | | | 67 | | |
| KHG26342 | | | 88 | | |
| KHG26344 | | | 58 | | |
| KHG26345 | | | 63 | | |

Considering that the cell viability of the control, which is treated with beta-amyloid (without any compounds according to the present invention), is 35% as shown in FIG. 1B, all the compounds shown in Table 2 can be considered to have meaningful effect of cell death suppression. In addition, even though the viability is less than 35%, such results are obtained when the compounds are used at a very low concentration such as 500 nM or less; therefore, if the compounds showing the viability of less than 35% can exhibits a meaningful effect when they used in a increased concentration.

What is claimed is:

1. A compound represented by chemical formula 1:

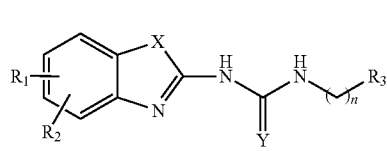

Chemical formula 1 wherein, X is selected from the group consisting of S, O, NH, and $NCH_3$;

Y is O or S;

$R_1$ and $R_2$ are independently selected from the group consisting of hydrogen, halogen atom, C1 to 5 linear or branched alkyl, and C1 to C5 alkoxy, $R_3$ is selected from the group consisting of OH, cyano, C1 to C5 alkoxy, $COOR_4$, tetrazole, phenyl, phenyl substituted with C1 to C5 linear or branched alkyl, and phenyl substituted with C1 to C5 linear or branched alkoxy, where $R_4$ is selected from the group consisting of hydrogen, C1 to C5 linear or branched alkyl, and an alkaline metal;

n is an integer ranging from 1 to 5; and with the proviso that 1) when X is $NCH_3$, Y is S, or at least one of $R_1$ and $R_2$ is selected from the group consisting of halogen atom, C1 to C5 linear or branched alkyl and C1 to C5 alkoxy, 2) when X and Y are S, at least one of $R_1$ and $R_2$ is selected from the group consisting of halogen atom, C1 to C5 linear or branched alkyl and C1 to C5 alkoxy, or $R_3$ is selected from the group consisting of phenyl, phenyl substituted with C1 to C5 linear or branched alkyl, phenyl substituted with C1 to C5 linear or branched alkoxy, cyano, C1 to C3 alkoxy, tetrazole, OH and $COOR_4$ (where, $R_4$ is selected from the group consisting of hydrogen, methyl, C3 to C5 linear or branched alkyl and K), and 3) when n is 1, X is O or $NCH_3$, Y is S, at least one of $R_1$ and $R_2$ is halogen atom, and $R_3$ is selected from the group consisting of OH, cyano, C1 to C5 alkoxy, $COOR_4$, tetrazole, phenyl, phenyl substituted with C1 to C5 linear or branched alkyl, phenyl substituted with C1 to C5 linear or branched alkoxy, where $R_4$ is selected from the group consisting of hydrogen, methyl, C3 to C5 linear or branched alkyl and an alkaline metal.

2. The compound of claim 1, wherein:
when n is 2 or 3, X is S, Y is O, and $R_1$ and $R_2$ are hydrogen, $R_3$ is selected from the group consisting of OH, cyano, C1 to C5 alkoxy, COOR$_4$, tetrazole, phenyl, phenyl substituted with C1 to C5 linear or branched alkyl, phenyl substituted with C1 to C5 linear or branched alkoxy, and $R_4$ is selected from the group consisting of C1 to C5 linear or branched alkyl and an alkaline metal.

3. The compound of any one of claim 1, wherein:
$R_1$ and $R_2$ are independently selected from the group consisting of H, F, Cl, C1 to C3 alkyl and C1 to C3 alkoxy;
$R_3$ is selected from the group consisting of OH, cyano, C1 to C5 alkoxy, COOR$_4$, tetrazole, phenyl, phenyl substituted with C1 to C5 linear or branched alkyl, phenyl substituted with C1 to C5 linear or branched alkoxy, where $R_4$ is selected from the group consisting of hydrogen, C1 to C5 linear or branched alkyl and K; and
n is an integer ranging from 1 to 3.

4. The compound of claim 1, wherein the compound is any one of compounds listed in following table 1-1.

TABLE 1-1

| Number of compound | X | Y | $R_1$ & $R_2$ | $(CH_2)_nR_3$ |
|---|---|---|---|---|
| KHG25948 | S | O | H, H | $CH_2C_6H_4$ (4-$CH_3$) |
| KHG25954 | S | O | H, H | $CH_2CO_2$(n-Bu) |
| KHG25956 | S | O | 6-F, H | $CH_2CO_2Et$ |
| KHG25989 | O | O | 6-Cl, H | $CH_2CO_2Et$ |
| KHG25990 | O | O | 6-Cl, H | $CH_2C_6H_4$ (4-$CH_3$) |
| KHG26004 | S | O | H, H | $CH_2CH_2CH_2CO_2Et$ |
| KHG26005 | S | O | H, H | $CH_2CH_2CO_2Et$ |
| KHG26019 | S | O | 6-$OCH_3$, H | $CH_2CO_2Et$ |
| KHG26027 | NH | O | H, H | $CH_2CH_2CO_2Et$ |
| KHG26028 | NH | O | H, H | $CH_2CH_2CH_2CO_2Et$ |
| KHG26030 | $NCH_3$ | O | H, H | $CH_2CH_2CO_2Et$ |
| KHG26031 | $NCH_3$ | O | H, H | $CH_2CH_2CH_2CO_2Et$ |
| KHG26096 | S | O | H, H | $CH_2CO_2K$ |
| KHG26172 | $NCH_3$ | O | H, H | $CH_2CO_2K$ |
| KHG26175 | S | O | 6-$OCH_3$, H | $CH_2CO_2K$ |
| KHG26176 | S | O | 6-OEt, H | $CH_2CO_2K$ |
| KHG26177 | S | O | 6-Cl, H | $CH_2CO_2K$ |
| KHG26178 | S | O | 4-Cl, H | $CH_2CO_2K$ |
| KHG26180 | S | O | 5-$CH_3$, 6-$CH_3$ | $CH_2CO_2K$ |
| KHG26216 | S | O | 6-$CH_3$, H | $CH_2CO_2K$ |
| KHG26217 | S | O | 4-$CH_3$, H | $CH_2CO_2K$ |
| KHG26220 | S | O | H, H | $CH_2CH_2CO_2K$ |
| KHG26221 | S | O | H, H | $CH_2CH_2CH_2CO_2K$ |
| KHG26222 | $NCH_3$ | O | H, H | $CH_2CH_2CO_2K$ |
| KHG26223 | $NCH_3$ | O | H, H | $CH_2CH_2CH_2CO_2K$ |
| KHG26279 | S | O | H, H | $CH_2CH_2OH$ |
| KHG26280 | $NCH_3$ | O | H, H | $CH_2CO_2H$ |
| KHG26303 | $NCH_3$ | S | H, H | $CH_2CO_2Et$ |
| KHG26305 | S | S | 6-$CH_3$, H | $CH_2CO_2Et$ |
| KHG26306 | S | S | 4-$CH_3$, H | $CH_2CO_2Et$ |
| KHG26307 | S | S | 5-$CH_3$, 6-$CH_3$ | $CH_2CO_2Et$ |
| KHG26308 | S | S | 6-$OCH_3$, H | $CH_2CO_2Et$ |
| KHG26309 | S | S | 6-OEt, H | $CH_2CO_2Et$ |
| KHG26310 | S | S | 6-F, H | $CH_2CO_2Et$ |
| KHG26311 | S | S | 6-Cl, H | $CH_2CO_2Et$ |
| KHG26312 | S | S | 4-Cl, H | $CH_2CO_2Et$ |
| KHG26316 | S | S | H, H | $CH_2CO_2H$ |
| KHG26332 | S | O | H, H | $CH_2CH_3$ |
| KHG26334 | $NCH_3$ | S | H, H | $CH_2CO_2H$ |
| KHG26335 | S | S | 5-$CH_3$, 6-$CH_3$ | $CH_2CO_2H$ |
| KHG26336 | S | S | 6-OEt, H | $CH_2CO_2H$ |
| KHG26340 | S | S | 4-$CH_3$, H | $CH_2CO_2H$ |
| KHG26341 | S | S | 6-Cl, H | $CH_2CO_2H$ |
| KHG26342 | S | O | H, H | $CH_2CN$ |
| KHG26344 | S | O | H, H | $CH_2CH_2OEt$ |
| KHG26345 | S | O | H, H | $CH_2$-tetrazolyl |
| KHG26346 | S | O | 6-$OCH_3$, H | $CH_2CO_2Et$ |
| KHG26347 | S | O | 6-OEt, H | $CH_2CO_2Et$ |
| KHG26348 | S | O | 6-OEt, H | $CH_2CO_2H$ |
| KHG26349 | S | O | 6-Cl, H | $CH_2CO_2Et$ |
| KHG26350 | S | O | 6-Cl, H | $CH_2CO_2H$ |

TABLE 1-1-continued

| Number of compound | X | Y | $R_1$ & $R_2$ | $(CH_2)_nR_3$ |
|---|---|---|---|---|
| KHG26351 | S | O | 4-Cl, H | $CH_2CO_2Et$ |
| KHG26352 | S | O | 4-Cl, H | $CH_2CO_2H$ |
| KHG26353 | S | O | 5-$CH_3$, 6-$CH_3$ | $CH_2CO_2Et$ |
| KHG26354 | S | O | 5-$CH_3$, 6-$CH_3$ | $CH_2CO_2H$ |
| KHG26355 | S | O | 6-$CH_3$, H | $CH_2CO_2H$ |
| KHG26356 | S | O | 4-$CH_3$, H | $CH_2CO_2H$ |
| KHG26357 | $NCH_3$ | O | H, H | $CH_2CH_2CO_2H$ |
| KHG26358 | $NCH_3$ | O | H, H | $CH_2CH_2CH_2CO_2H$. |

5. A composition comprising a compound represented by chemical formula 1 or a pharmaceutically-acceptable salt thereof as an active ingredient;

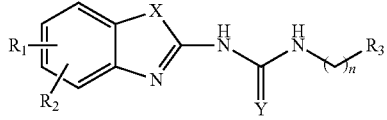

Chemical formula 1 where, X is selected from the group consisting of S, O, NH and $NCH_3$;

Y is O or S;

$R_1$ and $R_2$ are independently selected from the group consisting of hydrogen, halogen atom, C1 to 5 linear or branched alkyl and C1 to C5 alkoxy, $R_3$ is selected from the group consisting of OH, cyano, C1 to C5 alkoxy, COOR$_4$, tetrazole, phenyl, phenyl substituted with C1 to C5 linear or branched alkyl, phenyl substituted with C1 to C5 linear or branched alkoxy, and $R_4$ is selected from the group consisting of hydrogen, C1 to C5 linear or branched alkyl and an alkaline metal;

n is an integer ranging from 1 to 5; and with the proviso that 1) when X is $NCH_3$, Y is S, or at least one of $R_1$ and $R_2$ is selected from the group consisting of halogen atom, C1 to C5 linear or branched alkyl and C1 to C5 alkoxy, or 2) when X and Y are S, at least one of $R_1$ and $R_2$ is selected from the group consisting of halogen atom, C1 to C5 linear or branched alkyl and C1 to C5 alkoxy, or $R_3$ is selected from the group consisting of phenyl, phenyl substituted with C1 to C5 linear or branched alkyl, phenyl substituted with C1 to C5 linear or branched alkoxy, cyano, C1 to C3 alkoxy, tetrazole, OH and COOR$_4$ (where, $R_4$ is selected from the group consisting of hydrogen, methyl, C3 to C5 linear or branched alkyl and K), and 3) when n is 1, X is O or $NCH_3$, Y is S, at least one of $R_1$ and $R_2$ is halogen atom, and $R_3$ is selected from the group consisting of OH, cyano, C1 to C5 alkoxy, COOR$_4$, tetrazole, phenyl, phenyl substituted with C1 to C5 linear or branched alkyl, phenyl substituted with C1 to C5 linear or branched alkoxy, where $R_4$ is selected from the group consisting of hydrogen, methyl, C3 to C5 linear or branched alkyl and an alkaline metal.

6. The composition of claim 5, wherein the compound is any one of compounds listed in following table 1.

TABLE 1

| Number of compound | X | Y | $R_1$ & $R_2$ | $(CH_2)_nR_3$ |
|---|---|---|---|---|
| KHG25948 | S | O | H, H | $CH_2C_6H_4$ (4-$CH_3$) |
| KHG25954 | S | O | H, H | $CH_2CO_2$(n-Bu) |
| KHG25956 | S | O | 6-F, H | $CH_2CO_2Et$ |
| KHG25967 | S | O | H, H | $CH_2CO_2H$ |
| KHG25989 | O | O | 6-Cl, H | $CH_2CO_2Et$ |
| KHG25990 | O | O | 6-Cl, H | $CH_2C_6H_4$ (4-$CH_3$) |
| KHG26004 | S | O | H, H | $CH_2CH_2CH_2CO_2Et$ |
| KHG26005 | S | O | H, H | $CH_2CH_2CO_2Et$ |
| KHG26019 | S | O | 6-$OCH_3$, H | $CH_2CO_2Et$ |
| KHG26025 | S | O | H, H | $CH_2CH_2CH_2CO_2H$ |
| KHG26026 | S | O | H, H | $CH_2CH_2CO_2H$ |
| KHG26027 | NH | O | H, H | $CH_2CH_2CO_2Et$ |
| KHG26028 | NH | O | H, H | $CH_2CH_2CH_2CO_2Et$ |
| KHG26029 | $NCH_3$ | O | H, H | $CH_2CO_2Et$ |
| KHG26030 | $NCH_3$ | O | H, H | $CH_2CH_2CO_2Et$ |
| KHG26031 | $NCH_3$ | O | H, H | $CH_2CH_2CH_2CO_2Et$ |
| KHG26096 | S | O | H, H | $CH_2CO_2K$ |
| KHG26172 | $NCH_3$ | O | H, H | $CH_2CO_2K$ |
| KHG26175 | S | O | 6-$OCH_3$, H | $CH_2CO_2K$ |
| KHG26176 | S | O | 6-OEt, H | $CH_2CO_2K$ |
| KHG26177 | S | O | 6-Cl, H | $CH_2CO_2K$ |
| KHG26178 | S | O | 4-Cl, H | $CH_2CO_2K$ |
| KHG26180 | S | O | 5-$CH_3$, 6-$CH_3$ | $CH_2CO_2K$ |
| KHG26216 | S | O | 6-$CH_3$, H | $CH_2CO_2K$ |
| KHG26217 | S | O | 4-$CH_3$, H | $CH_2CO_2K$ |
| KHG26220 | S | O | H, H | $CH_2CH_2CO_2K$ |
| KHG26221 | S | O | H, H | $CH_2CH_2CH_2CO_2K$ |
| KHG26222 | $NCH_3$ | O | H, H | $CH_2CH_2CO_2K$ |
| KHG26223 | $NCH_3$ | O | H, H | $CH_2CH_2CH_2CO_2K$ |
| KHG26279 | S | O | H, H | $CH_2CH_2OH$ |
| KHG26280 | $NCH_3$ | O | H, H | $CH_2CO_2H$ |
| KHG26303 | $NCH_3$ | S | H, H | $CH_2CO_2Et$ |
| KHG26304 | S | S | H, H | $CH_2CO_2Et$ |
| KHG26305 | S | S | 6-$CH_3$, H | $CH_2CO_2Et$ |
| KHG26306 | S | S | 4-$CH_3$, H | $CH_2CO_2Et$ |
| KHG26307 | S | S | 5-$CH_3$, 6-$CH_3$ | $CH_2CO_2Et$ |
| KHG26308 | S | S | 6-$OCH_3$, H | $CH_2CO_2Et$ |
| KHG26309 | S | S | 6-OEt, H | $CH_2CO_2Et$ |
| KHG26310 | S | S | 6-F, H | $CH_2CO_2Et$ |
| KHG26311 | S | S | 6-Cl, H | $CH_2CO_2Et$ |
| KHG26312 | S | S | 4-Cl, H | $CH_2CO_2Et$ |
| KHG26316 | S | S | H, H | $CH_2CO_2H$ |
| KHG26332 | S | O | H, H | $CH_2CH_3$ |
| KHG26334 | $NCH_3$ | S | H, H | $CH_2CO_2H$ |
| KHG26335 | S | S | 5-$CH_3$, 6-$CH_3$ | $CH_2CO_2H$ |
| KHG26336 | S | S | 6-OEt, H | $CH_2CO_2H$ |
| KHG26340 | S | S | 4-$CH_3$, H | $CH_2CO_2H$ |
| KHG26341 | S | S | 6-Cl, H | $CH_2CO_2H$ |
| KHG26342 | S | O | H, H | $CH_2CN$ |
| KHG26344 | S | O | H, H | $CH_2CH_2OEt$ |
| KHG26345 | S | O | H, H | $CH_2$-tetrazolyl |
| KHG26346 | S | O | 6-$OCH_3$, H | $CH_2CO_2H$ |
| KHG26347 | S | O | 6-OEt, H | $CH_2CO_2Et$ |
| KHG26348 | S | O | 6-OEt, H | $CH_2CO_2H$ |
| KHG26349 | S | O | 6-Cl, H | $CH_2CO_2Et$ |
| KHG26350 | S | O | 6-Cl, H | $CH_2CO_2H$ |
| KHG26351 | S | O | 4-Cl, H | $CH_2CO_2Et$ |
| KHG26352 | S | O | 4-Cl, H | $CH_2CO_2H$ |
| KHG26353 | S | O | 5-$CH_3$, 6-$CH_3$ | $CH_2CO_2Et$ |
| KHG26354 | S | O | 5-$CH_3$, 6-$CH_3$ | $CH_2CO_2H$ |
| KHG26355 | S | O | 6-$CH_3$, H | $CH_2CO_2H$ |
| KHG26356 | S | O | 4-$CH_3$, H | $CH_2CO_2H$ |
| KHG26357 | $NCH_3$ | O | H, H | $CH_2CH_2CO_2H$ |
| KHG26358 | $NCH_3$ | O | H, H | $CH_2CH_2CH_2CO_2H$. |

7. The composition of claim 5, wherein the composition is formulated as plaster, granule, lotion, powder, syrup, liquid, solution, aerosol, ointment, fluidextract, emulsion, suspension, infusion, tablet, injection, capsule, or pill.

8. A food comprising a compound represented by chemical formula 1 or a pharmaceutically-acceptable salt thereof as an active ingredient;

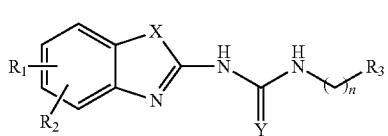

Chemical formula 1 where, X is selected from the group consisting of S, O, NH and $NCH_3$;

Y is O or S;

$R_1$ and $R_2$ are independently selected from the group consisting of hydrogen, halogen atom, C1 to 5 linear or branched alkyl and C1 to C5 alkoxy, $R_3$ is selected from the group consisting of OH, cyano, C1 to C5 alkoxy, $COOR_4$, tetrazole, phenyl, phenyl substituted with C1 to C5 linear or branched alkyl, phenyl substituted with C1 to C5 linear or branched alkoxy, and $R_4$ is selected from the group consisting of hydrogen, C1 to C5 linear or branched alkyl and an alkaline metal;

n is an integer ranging from 1 to 5; and with the proviso that 1) when X is $NCH_3$, Y is S, or at least one of $R_1$ and $R_2$ is selected from the group consisting of halogen atom, C1 to C5 linear or branched alkyl and C1 to C5 alkoxy, or 2) when X and Y are S, at least one of $R_1$ and $R_2$ is selected from the group consisting of halogen atom, C1 to C5 linear or branched alkyl and C1 to C5 alkoxy, or $R_3$ is selected from the group consisting of phenyl, phenyl substituted with C1 to C5 linear or branched alkyl, phenyl substituted with C1 to C5 linear or branched alkoxy, cyano, C1 to C3 alkoxy, tetrazole, OH and COOR4 (where, R4 is selected from the group consisting of hydrogen, methyl, C3 to C5 linear or branched alkyl and K), and 3) when n is 1, X is O or $NCH_3$, Y is S, at least one of $R_1$ and $R_2$ is halogen atom, and $R_3$ is selected from the group consisting of OH, cyano, C1 to C5 alkoxy, $COOR_4$, tetrazole, phenyl, phenyl substituted with C1 to C5 linear or branched alkyl, phenyl substituted with C1 to C5 linear or branched alkoxy, where $R_4$ is selected from the group consisting of hydrogen, methyl, C3 to C5 linear or branched alkyl and an alkaline metal.

9. The compound of claim 2, wherein:

$R_3$ is selected from the group consisting of OH, cyano, C1 to C5 alkoxy, $COOR_4$, tetrazole, phenyl, phenyl substituted with C1 to C5 linear or branched alkyl, phenyl substituted with C1 to C5 linear or branched alkoxy, where $R_4$ is selected from the group consisting of hydrogen, C1 to C5 linear or branched alkyl and K; and n is an integer ranging from 1 to 3.

10. The composition of claim 6, wherein the composition is formulated as plaster, granule, lotion, powder, syrup, liquid, solution, aerosol, ointment, fluidextract, emulsion, suspension, infusion, tablet, injection, capsule, or pill.

* * * * *